US010486148B2

(12) United States Patent
Montgomery et al.

(10) Patent No.: US 10,486,148 B2
(45) Date of Patent: Nov. 26, 2019

(54) NI(0) CATALYSTS

(71) Applicants: THE REGENTS OF THE UNIVERSITY OF MICHIGAN, Ann Arbor, MI (US); FUNDACIÓ INSTITUT CATALÀ D'INVESTIGACIÓ QUÍMICA (ICIQ), Tarragona (ES)

(72) Inventors: John Montgomery, Ann Arbor, MI (US); Alex J. Nett, Ann Arbor, MI (US); Michael Robo, Ann Arbor, MI (US); Santiago Cañellas Roman, Tarragona (ES)

(73) Assignees: THE REGENTS OF THE UNIVERSITY OF MICHIGAN, Ann Arbor, MI (US); FUNDACIO INSTITUT CATALA D'INVESTIGACIO QUIMICA (ICIQ), Tarragona (ES)

( * ) Notice: Subject to any disclaimer, the term of this patent is extended or adjusted under 35 U.S.C. 154(b) by 0 days.

(21) Appl. No.: 15/763,468

(22) PCT Filed: Sep. 30, 2016

(86) PCT No.: PCT/US2016/054628
§ 371 (c)(1),
(2) Date: Mar. 27, 2018

(87) PCT Pub. No.: WO2017/059181
PCT Pub. Date: Apr. 6, 2017

(65) Prior Publication Data
US 2018/0264448 A1 Sep. 20, 2018

Related U.S. Application Data

(60) Provisional application No. 62/235,376, filed on Sep. 30, 2015.

(51) Int. Cl.
*B01J 31/22* (2006.01)
*C07B 37/02* (2006.01)
*C07B 37/04* (2006.01)
*C07B 43/04* (2006.01)
*C07B 47/00* (2006.01)
*C07C 1/32* (2006.01)
*C07C 17/35* (2006.01)
*C07C 209/10* (2006.01)
*C07D 295/073* (2006.01)
*C07F 7/18* (2006.01)
*C07F 15/04* (2006.01)
*C07J 51/00* (2006.01)

(52) U.S. Cl.
CPC ....... *B01J 31/2291* (2013.01); *B01J 31/2273* (2013.01); *C07B 37/02* (2013.01); *C07B 37/04* (2013.01); *C07B 43/04* (2013.01); *C07B 47/00* (2013.01); *C07C 1/321* (2013.01); *C07C 17/35* (2013.01); *C07C 209/10* (2013.01); *C07D 295/073* (2013.01); *C07F 7/188* (2013.01); *C07F 15/04* (2013.01); *C07J 51/00* (2013.01); *B01J 2231/323* (2013.01); *B01J 2231/4227* (2013.01); *B01J 2231/4283* (2013.01); *B01J 2231/4288* (2013.01); *B01J 2531/847* (2013.01); *B01J 2540/10* (2013.01)

(58) Field of Classification Search
None
See application file for complete search history.

(56) References Cited

U.S. PATENT DOCUMENTS

| 5,007,414 A | 4/1991 | Sexton |
| 2006/0111593 A1 | 5/2006 | Itahashi et al. |
| 2009/0221419 A1 | 9/2009 | Pears et al. |
| 2011/0218306 A1 | 9/2011 | Matyjaszewski et al. |

OTHER PUBLICATIONS

Álvarez-Bercedo et al., Ni-catalyzed reduction of inert C-O bonds: a new strategy for using aryl ethers as easily removable directing groups, J. Am. Chem. Soc., 132(49):17352-3 (2010).
Amarasinghe et al., Structure of an $\eta^1$ Nickel O-Enolate: Mechanistic Implications in Catalytic Enyne Cyclizations, 20(3):370-2 (2001).
Arduengo et al., Electronic stabilization of nucleophilic carbenes, J. Am. Chem. Soc., 114(14):5530-4 (1992).
Beaver et al., Ni(II) salts and 2-propanol effect catalytic reductive coupling of epoxides and alkynes, Org. Lett., 13(15):4140-3 (2011).
Berini et al., Rapid and selective catalytic oxidation of secondary alcohols at room temperature by using (N-heterocyclic carbene)-ni(0) systems, Chemistry, 16(23):6857-60 (2010).
Bower et al., Catalytic C-C coupling via transfer hydrogenation: reverse prenylation, crotylation, and allylation from the alcohol or aldehyde oxidation level, J. Am. Chem. Soc., 129(49):15134-5 (2007).
Bower et al., Catalytic carbonyl addition through transfer hydrogenation: a departure from preformed organometallic reagents, Angew. Chem. Int. Ed. Engl., 48(1):34-46 (2009).
Braddock et al., The Cyclopropylmethylsilane Terminated Prins Reaction: Stereoelectronic Controlled Formation of (E)-Skipped Dienes, Synlett., 2001(12):1909-12 (2001).

(Continued)

*Primary Examiner* — Samantha L Shterengarts
(74) *Attorney, Agent, or Firm* — Marshall, Gerstein & Borun LLP

(57) ABSTRACT

Provided herein are nickel(O) catalysts that are stable when exposed to air and can be used to catalyze the formation of a C—C, C—O, or C—N bond.

20 Claims, 2 Drawing Sheets

(56) References Cited

OTHER PUBLICATIONS

Castaing et al., 2-Aminobenzaldehydes as versatile substrates for rhodium-catalyzed alkyne hydroacylation: application to dihydroquinolone synthesis, Angew. Chem. Int. Ed. Engl., 52(50):13280-3 (2013).
Chaplin et al., Intermolecular hydroacylation: high activity rhodium catalysts containing small-bite-angle diphosphine ligands, J. Am. Chem. Soc., 134(10):4885-97 (2012).
Chen et al., Alkyne hydroacylation: switching regioselectivity by tandem ruthenium catalysis, J. Am. Chem. Soc., 137(9):3157-60 (2015).
Chen et al., Regioselective hydroacylation of 1,3-dienes by cobalt catalysis, J. Am. Chem. Soc., 136(10):3772-5 (2014).
Clement et al., Zerovalent N-Heterocyclic Carbene Complexes of Palladium and Nickel Dimethyl Fumarate: Synthesis, Structure, and Dynamic Behavior, Organometallics, 25(17):4155-65 (2006).
Cornella et al., Combined experimental and theoretical study on the reductive cleavage of inert C-O bonds with silanes: ruling out a classical Ni(0)/Ni(II) catalytic couple and evidence for Ni(I) intermediates, J. Am. Chem. Soc., 135(5):1997-2009 (2013).
Cámpora et al., Synthesis and aldol reactivity of o- and C-enolate complexes of nickel, J. Am. Chem. Soc., 125(6):1482-3 (2003).
Das et al., Stereoselective alkylation of allylic alcohols: tandem ethylation and functionalization, Angew. Chem. Int. Ed. Engl., 50(40):9459-61 (2011).
Gandeepan et al., Cobalt catalysis involving ? components in organic synthesis, Acc. Chem. Res., 48(4):1194-206 (2015).
Gao et al., Total synthesis of 6-deoxyerythronolide B via C-C bond-forming transfer hydrogenation, J. Am. Chem. Soc., 135(11):4223-6 (2013).
Herath et al., Fully intermolecular nickel-catalyzed three-component couplings via internal redox, J. Am. Chem. Soc., 130(2):469-71 (2008).
Herath et al., Highly chemoselective and stereoselective synthesis of z-enol silanes, J. Am. Chem. Soc., 130(26):8132-3 (2008).
Ho et al., Alpha-olefins as alkenylmetal equivalents in catalytic conjugate addition reactions, Angew. Chem. Int. Ed. Engl., 47(10):1893-5 (2008).
Ho et al., Catalytic asymmetric hydroalkenylation of vinylarenes: electronic effects of substrates and chiral N-heterocyclic carbene ligands, Angew. Chem. Int. Ed. Engl., 54(15):4512-6 (2015).
Ho et al., Catalytic intermolecular tail-to-tail hydroalkenylation of styrenes with ? olefins: regioselective migratory insertion controlled by a nickel/N-heterocyclic carbene, Angew Chem. Int. Ed. Engl., 49(48):9182-6 (2010).
Hoshimoto et al., Catalytic Transformation of Aldehydes with Nickel Complexes through ?(2) Coordination and Oxidative Cyclization, Acc. Chem. Res., 48(6):1746-55 (2015).
Hoshimoto et al., Synthesis of five- and six-membered benzocyclic ketones through intramolecular alkene hydroacylation catalyzed by nickel(0)/N-heterocyclic carbenes, Angew. Chem. Int. Ed. Engl., 51(43):10812-5 (2012).
Iglesias et al., Synthesis, Structural Characterization, and Catalytic Activity of IPrNi(styrene)2 in the Amination of Aryl Tosylates, Organometallics, 31(17):6312-6 (2012).
Ikeda, Nickel-catalyzed coupling of carbonyl compounds and alkynes or 1,3-dienes: an efficient method for the preparation of allylic, homoallylic, and bishomoallylic alcohols, Angew. Chem. Int. Ed. Engl., 42(42):5120-2 (2003).
International Application No. PCT/US16/54628, International Preliminary Report on Patentability, dated Apr. 3, 2018.
International Application No. PCT/US16/54628, International Search Report and Written Opinion, dated Dec. 29, 2016.
Jackson et al., Mechanistic Basis for Regioselection and Regiodivergence in Nickel-Catalyzed Reductive Couplings, Acc. Chem. Res., 48(6):1736-45 (2015).
Jamal et al., Functionalization of the Benzylic C-H Bonds in Azaarenes by Cobalt-Catalyzed 1,4-Addition to Enones, Eur. J. Org. Chem., 2014(33):7343-6 (Nov. 2014).
Jang et al., Catalytic C-C bond formation via capture of hydrogenation intermediates, Acc. Chem. Res., 37(9):653-61 (2004).
Jarvis et al., Syntheses and structures of nickel(0) complexes containing the methyl methacrylate monomer as ligand, J.Chem. Soc. Dalton Trans., (12):2033-40 (1995).
Jeganmohan et al., Cobalt- and nickel-catalyzed regio- and stereoselective reductive coupling of alkynes, allenes, and alkenes with alkenes, Chemistry, 14(35):10876-86 (2008).
Jeso et al., Total synthesis of lehualide B by allylic alcohol-alkyne reductive cross-coupling, J. Am. Chem. Soc., 132(33):11422-4 (2010).
Kelley et al., Nickel-mediated hydrogenolysis of C-O bonds of aryl ethers: what is the source of the hydrogen?, J. Am. Chem. Soc., 134912):5480-3 (2012).
Kolundzic et al., Synthesis of substituted 1,4-dienes by direct alkylation of allylic alcohols, J. Am. Chem. Soc., 129(49):15112-3 (2007).
Kou et al., Rh(I)-catalyzed intermolecular hydroacylation: enantioselective cross-coupling of aldehydes and ketoamides, J. Am. Chem. Soc., 136(26):9471-6 (2014).
Li et al., Evolution of efficient strategies for enone-alkyne and enal-alkyne reductive couplings, J. Am. Chem. Soc., 131(46):17024-9 (2009).
Lysenko et al., Low-valent titanium-mediated stereoselective alkylation of allylic alcohols, J. Am. Chem. Soc., 130(47):15997-6002 (2008).
Macklin et al., Convergent and stereospecific synthesis of complex skipped polyenes and polyunsaturated fatty acids, Nat. Chem., 2(8):638-43 (2010).
Mahandru et al., Cascade cyclizations and couplings involving nickel enolates, J. Am. Chem. Soc., 125(44):13481-5 (2003).
Mans et al., Ethylene in organic synthesis. Repetitive hydrovinylation of alkenes for highly enantioselective syntheses of pseudopterosins, J. Am. Chem. Soc., 133(15):5776-9 (2011).
Montgomery et al., "Nickel-catalyzed reductive couplings of aldehydes and alkynes", pp. 1-23, IN: Krische (ed.), Metal Catalyzed Reductive C-C Bond Formation: A Departure from Preformed Organometallic Reagents, Springer-Verlag Berlin Heidelberg (2007).
Montgomery, "Organonickel Chemistry" pp. 319-428 IN: Lipshutz (ed.), Organometallics in Synthesis, Fourth Manual, Hoboken, NJ: Wiley, (2013).
Montgomery, Nickel-catalyzed reductive cyclizations and couplings, Angew. Chem. Int. Ed. Engl., 43(30):3890-908 (2004).
Moslin et al., Regioselectivity and enantioselectivity in nickel-catalysed reductive coupling reactions of alkynes, Chem. Commun. (Camb.), 43:4441-9 (2007).
Nakai et al., Nickel-catalyzed redox-economical coupling of alcohols and alkynes to form allylic alcohols, J. Am. Chem. Soc., 136(22):7797-800 (2014).
Ngai et al., Hydrogen-mediated C-C bond formation: a broad new concept in catalytic C-C coupling, J. Org. Chem., 72(4):1063-72 (2007).
Ohashi et al., Nickel-catalyzed formation of cyclopentenone derivatives via the unique cycloaddition of a,B-unsaturated phenyl esters with alkynes, J. Am. Chem. Soc., 133(38):14900-3 (2011).
Patman et al., Direct vinylation of alcohols or aldehydes employing alkynes as vinyl donors: a ruthenium catalyzed C-C bond-forming transfer hydrogenation, J. Am. Chem. Soc., 131(6):2066-7 (2009).
Prades et al., Well-Defined and Robust Rhodium Catalysts for the Hydroacylation of Terminal and Internal Alkenes, Angew. Chem. Int. Ed. Engl., 54(29):8520-4 (2015).
Qian et al., Catalytic cross deoxygenative and dehydrogenative coupling of aldehydes and alkenes: a redox-neutral process to produce skipped dienes, Chem. Commun. (Camb.), 49(84):9839-41 (2013).
Rajanbabu, Asymmetric hydrovinylation reaction, Chem. Rev., 103(8):2845-60 (2003).
RajanBabu, In Pursuit of an Ideal Carbon-Carbon Bond-Forming Reaction: Development and Applications of the Hydrovinylation of Olefins, Synlett, 2009(6):853-85 (2009).

(56) References Cited

OTHER PUBLICATIONS

Sergeev et al., Selective, nickel-catalyzed hydrogenolysis of aryl ethers, Science, 332(6028):43943 (2011).

Sharma et al., Asymmetric hydrovinylation of unactivated linear 1,3-dienes, J. Am. Chem. Soc., 132(10):3295-7 (2010).

Six, Titanium-Mediated Carboxylation of Alkynes With Carbon Dioxide, Eur. J. Org Chem., 2003(7):1157-71 (2003).

Skucas et al., Enantiomerically enriched allylic alcohols and allylic amines via C-C bond-forming hydrogenation: asymmetric carbonyl and imine vinylation, Acc. Chem. Res., 40(12):1394-401 (2007).

Sprengers et al., Synthesis and Crystal Structures of Zerovalent Platinum ?2-Fumarate Bis(norbornene) Complexes and Their Application as Hydrosilylation Catalysts, Organometallics, 23(13):3117-25 (2004).

Standley et al., Nickel Catalysis: Synergy between Method Development and Total Synthesis, Acc. Chem. Res., 48(5):1503-14 (2015).

Tamaki et al., Synthesis and reactivity of six-membered oxa-nickelacycles: a ring-opening reaction of cyclopropyl ketones, Chemistry, 15(39):10083-91 (2009).

Thadani et al., Stereospecific synthesis of highly substituted skipped dienes through multifunctional palladium catalysis, Org. Lett., 4(24):4317-20 (2002).

Tobisu et al., Nickel-catalyzed reductive cleavage of aryl alkyl ethers to arenes in absence of external reductant, Chem. Sci., 6:3410-4 (2015).

Trost et al., Mechanistic dichotomy in CpRu(CH(3)CN)(3)PF(6) catalyzed enyne cycloisomerizations, J. Am. Chem. Soc., 124(18):5025-36 (2002).

Trost et al., Ru-catalyzed alkene-alkyne coupling. Total synthesis of amphidinolide P, J. Am. Chem. Soc., 127(50):17921-37 (2005).

Trost et al., Ruthenium-Catalyzed Cycloisomerization of 1,6-Enynes Initiated by C?H Activation, J. Am. Chem. Soc., 121(41):9728-9 (1999).

Trost et al., Ruthenium-catalyzed reactions—a treasure trove of atom-economic transformations, Angew. Chem. Int. Ed. Engl., 44(41):6630-66 (2005).

Yang et al., Cobalt-Catalyzed Intermolecular Hydroacylation of Olefins through Chelation-Assisted Imidoyl C-H Activation, ACS Catal., 5(5):3054-7 (2015).

Yatagai, New procedure for synthesis of 1,4-dienes and monoolefins via methylcopper-induced cross-coupling of alkenylboranes with organic halides, J. Org. Chem., 45(9):1640-4 (1980).

Zhang et al., All-carbon quaternary centers via catalytic asymmetric hydrovinylation. New approaches to the exocyclic side chain stereochemistry problem, J. Am. Chem. Soc., 128(17):5620-1 (2006).

NI(0) CATALYSTS

STATEMENT OF GOVERNMENT SUPPORT

The invention was made with support from grant no. CHE-1265491, awarded by the National Science Foundation. The government has certain rights in this invention.

BACKGROUND

Previous reports described broad usage of nickel(0) complexes of N-heterocyclic carbene (NHC) ligands that are prepared either in situ from air-sensitive precursors or that are prepared and handled in an inert atmosphere glovebox. Nickel(0) NHC complexes where dimethyl fumarate stabilizes the complex and provides air stability are known, but the stabilizing dimethyl fumarate renders the catalysts too stable and inactive for most applications. Many examples of air-stable Ni(II) catalysts are known, but they typically do not involve NHC ligands, and they require reduction to the active Ni(0) form. To date, there are no examples of moderately air-stable Ni(0) complexes of NHC ligands that display good catalytic reactivity in transformations of broad interest to the pharmaceutical or polymer industries.

SUMMARY

Provided herein are Ni(0) catalysts having a structure of formula (I) or (II):

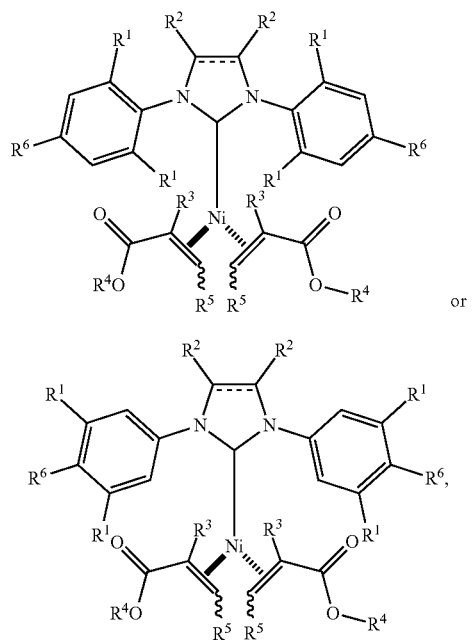

wherein the dashed line is an optional double bond; each $R^1$ is independently selected from the group consisting of H, $C_{1-8}$alkyl and $C_{1-2}$alkylenearyl; each $R^2$ is independently selected from the group consisting of H, halo, $C_{1-3}$alkyl, and aryl, or both $R^2$ together with the carbons to which they are attached form a 6-membered ring; each $R^3$ is the same and is H, $C_{1-4}$alkyl, or aryl; each $R^4$ is the same and is $C_{1-4}$alkyl, $C_{0-2}$alkylene-aryl or $C_{0-2}$alkylene-$C_{2-8}$alkene; each $R^5$ is the same and is H, $C_{1-6}$alkyl, aryl, $CO_2C_{0-2}$alkylene-aryl, $CO_2C_{0-2}$alkylene-$C_{2-8}$alkene, or $CO_2C_{2-6}$alkyl; and each $R^6$ is the same and is H, $C_{1-6}$alkyl, $C_{1-6}$alkoxy, or O-aryl, with the proviso that at least one of $R^1$ and $R^6$ is not H. In some cases, the dashed line is a double bond. In some cases, each $R^1$ is the same. In some cases, $R^1$ is selected from the group consisting of methyl, ethyl, propyl, isopropyl, butyl, sec-butyl, t-butyl, isobutyl, pentyl, 3-pentyl, and diphenylmethyl. In some cases, each $R^1$ is isopropyl. In some cases, $R^1$ is H. In some cases, each $R^2$ is the same. In some cases, each $R^2$ is selected from H, chloro, and methyl. In some cases, both $R^2$ together with the carbons to which they are attached form a 5- to 7-membered ring. In some cases, $R^3$ is aryl. In some cases, $R^3$ is phenyl. In some cases, $R^3$ is $C_{1-4}$alkyl. In some cases, $R^3$ is methyl or ethyl. In some cases, $R^3$ is H. In some cases, $R^4$ is $C_{0-2}$alkylene-aryl. In some cases, $R^4$ is $C_1$alkylene-aryl. In some cases, the aryl of $R^4$ comprises phenyl or naphthyl. In some cases, $R^4$ is toluyl, methoxyphenyl, trialkylphenyl (e.g., trimethylphenyl or triisopropylphenyl), $MeCO_2$-phenyl, or phenyl. In some cases, $R^4$ is $C_{0-2}$alkylene-$C_{2-8}$alkene. In some cases, $R^4$ is $C_1$alkylene-$C_{2-8}$alkene. In some cases, $R^4$ is $C_0$alkylene-$C_{2-8}$alkene. In some cases, the $C_{2-8}$alkene is $C_2$alkene. In some cases, $R^4$ is $C_{2-6}$alkyl, such as isopropyl or t-butyl. In some cases, $R^5$ is H. In some cases, $R^5$ is $C_{1-6}$alkyl. In some cases, $R^5$ is aryl. In some cases, $R^5$ is $CO_2C_{0-2}$alkylene-aryl, $CO_2C_{0-2}$alkylene-$C_{2-8}$alkene, or $CO_2C_{2-6}$alkyl. In some cases, $R^5$ is $CO_2$-aryl, and in some cases the aryl is toluyl, methoxyphenyl, trialkylphenyl (e.g., trimethylphenyl or triisopropylphenyl), or $CO_2Me$-phenyl. In some cases, $R^5$ is $CO_2C_{2-6}$alkyl (e.g., $CO_2$isopropyl or $CO_2$t-butyl). In some cases, $R^5$ is $C_0$alkylene-$C_{2-8}$alkene. In some cases, $R^6$ is H. In some cases, $R^6$ is $C_{1-6}$alkyl. In some cases, $R^6$ is $C_{1-6}$alkoxy. In some cases, $R^6$ is O-aryl. In some cases, the catalyst has a structure of formula (I). In some cases, the catalyst has a structure of formula (II).

Further provided are methods of using the catalysts as disclosed herein to catalyze the formation of a C—C, C—N, or C—O bond. In some cases, the bond formation can occur at room temperature or at a temperature of less than 50° C. In some cases, the catalyst can be present in an amount of about 0.1 mol % to 20 mol %. In some cases, the catalyst catalyzes the C—N bond formation in a Buchwald-Hartwig reaction between (a) Ar—X or Het-X and (b) an amine, wherein Ar is aryl, Het is heteroaryl, and X is halide, sulfonate, or $C_{1-8}$alkyl-C(O)—O. In some cases, the catalyst catalyzes the C—C bond formation in a Sukuzi reaction between (a) Ar—X or Het-X and (b) a boronic acid, boronic ester, or a trifluoroborate, wherein Ar is aryl, Het is heteroaryl, and X is halide, sulfonate, or $C_{1-8}$alkyl-C(O)—O. In some cases, the catalyst catalyzes the C—O bond formation in a Buchwald-Hartwig reaction between (a) Ar—X or Het-X and (b) a hydroxyl compound, wherein Ar is aryl, Het is heteroaryl, and X is halide, sulfonate, or $C_{1-8}$alkyl-C(O)—O.

DETAILED DESCRIPTION

Figure 1:
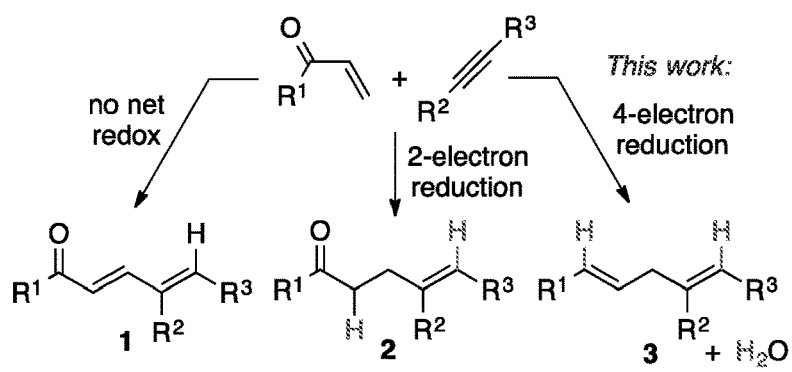
FIG. 1 shows a scheme of various reactions between an enal and an alkyne.

Provided herein are Ni(0) catalysts that can be used in the coupling reaction of a variety of starting materials, to form C—C, C—N, and C—O bonds. These catalysts are stable when exposed to air for short periods of time (e.g., 15 minutes or less) and still exhibit catalytic activity. In some cases, these catalysts are stable when exposed to air for up to three hours. This stability is in contrast to previously reported Ni(0) catalysts. In the past, Ni(0) catalysts would need to be generated in situ due to their instability from the precursor Ni(II) version.

Thus, as provided herein are Ni(0) catalysts of formula (I) or (II):

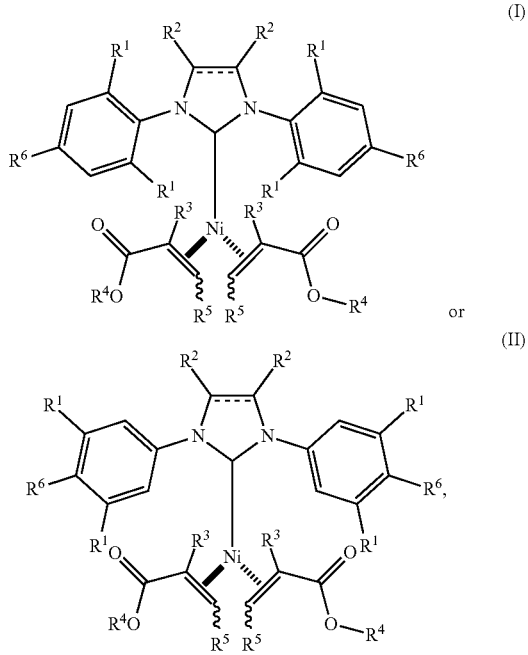

wherein the dashed line is an optional double bond; each $R^1$ is independently selected from the group consisting of H, $C_{1-8}$alkyl and $C_{1-2}$alkylenearyl; each $R^2$ is independently selected from the group consisting of H, halo, $C_{1-3}$alkyl, and aryl, or both $R^2$ together with the carbons to which they are attached form a 6-membered ring; each $R^3$ is the same and is H, $C_{1-4}$alkyl, or aryl; each $R^4$ is the same and is $C_{1-6}$alkyl, $C_{0-2}$alkylene-aryl or $C_{0-2}$alkylene-$C_{2-8}$alkene; each $R^5$ is the same and is H, $C_{1-6}$alkyl, aryl, $CO_2C_{0-2}$alkylene-aryl, $CO_2C_{0-2}$alkylene-$C_{2-8}$alkene, or $CO_2C_{2-6}$alkyl; and each $R^6$ is the same and is H, $C_{1-6}$alkyl, $C_{1-6}$alkoxy, or O-aryl, with the proviso that at least one of $R^1$ and $R^6$ is not H.

As used herein, the term "alkyl" refers to refers to straight chained and branched hydrocarbon groups, including but not limited to, methyl, ethyl, n-propyl, i-propyl, n-butyl, sec-butyl, t-butyl, n-pentyl, 3-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethybutyl. The term $C_{m-n}$ means the alkyl group has "m" to "n" carbon atoms. The term "alkylene" refers to an alkyl group having a substituent. An alkyl, e.g., methyl, or alkylene, e.g., —$CH_2$—, group can be substituted with one or more, and typically one to three, of independently selected halo, trifluoromethyl, trifluoromethoxy, hydroxy, alkoxy, nitro, cyano, alkylamino, or amino groups, for example. The term "alkene" refers to an alkyl group that has at least one double bond.

As used herein, the term "aryl" refers to a monocyclic or polycyclic aromatic group, preferably a monocyclic or bicyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, groups independently selected from, for example, halo, alkyl, alkenyl, —$OCF_3$, —$NO_2$, —CN, —NC, —OH, alkoxy, amino, alkylamino, —$CO_2H$, —$CO_2$alkyl, —OCOalkyl, aryl, heteroaryl, and O-aryl.

As used herein, the term "heteroaryl" refers to a monocyclic or polycyclic ring system (for example, bicyclic) containing one or two aromatic rings and containing at least one nitrogen, oxygen, or sulfur atom in an aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl group has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four, substituents selected from, for example, halo, alkyl, alkenyl, —$OCF_3$, —$NO_2$, —CN, —NC, —OH, alkoxy, amino, alkylamino, —$CO_2H$, —$CO_2$alkyl, —OCOalkyl, aryl, heteroaryl, and O-aryl.

Some specific catalysts contemplated include

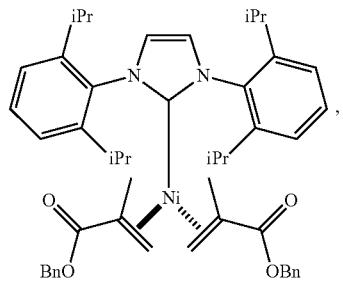

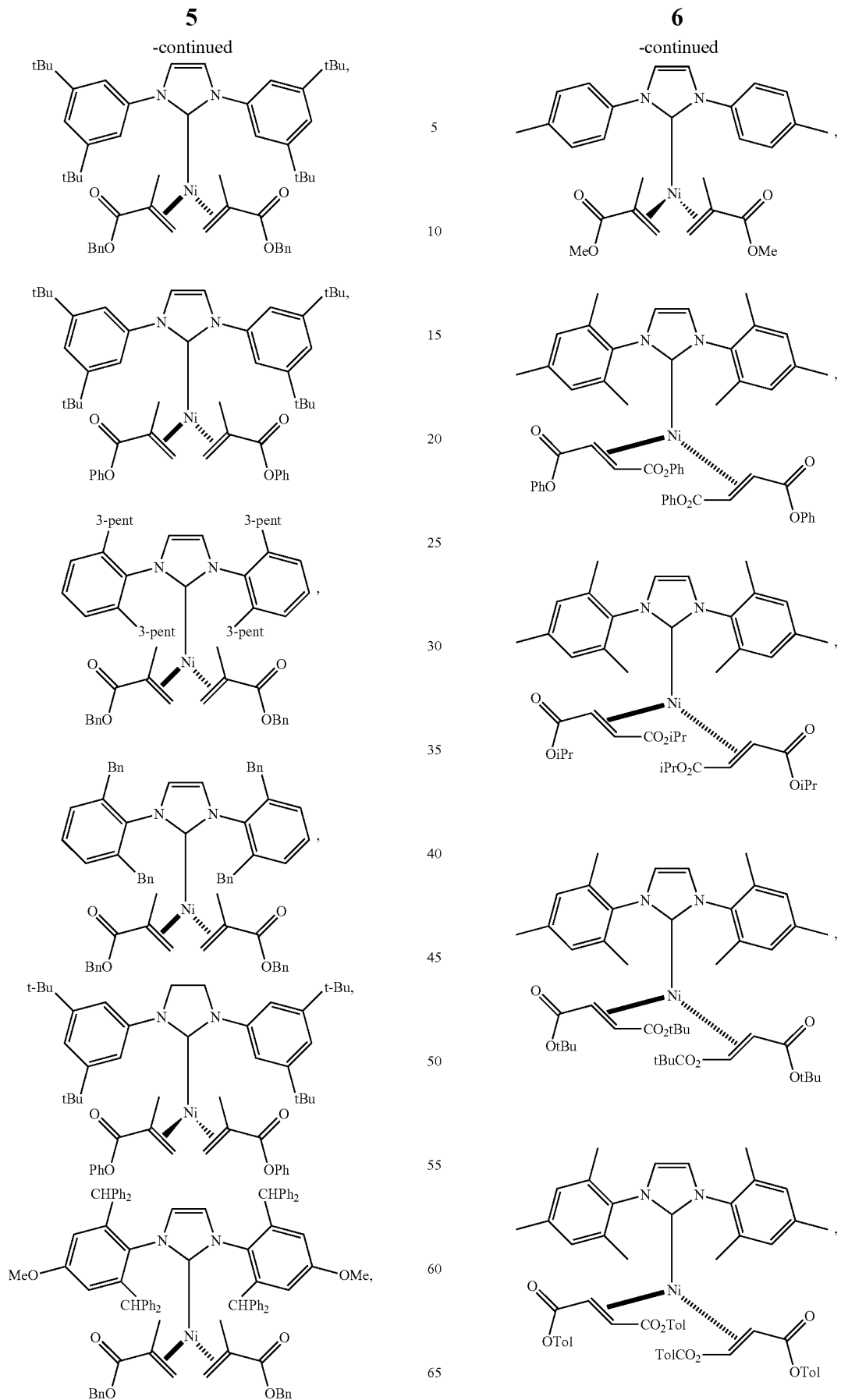

-continued

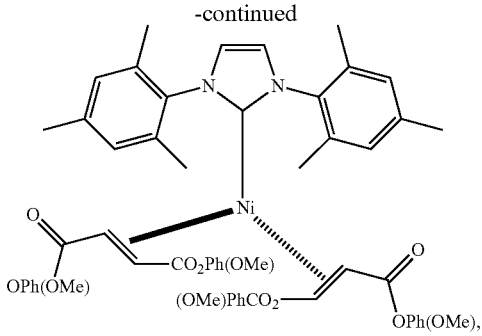

and

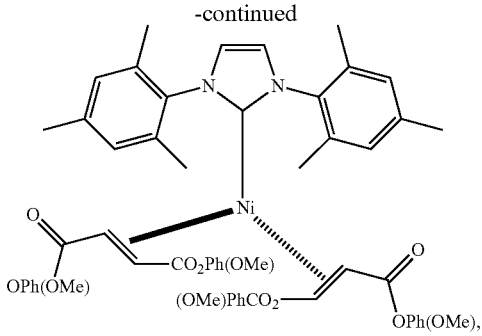

wherein Tol is

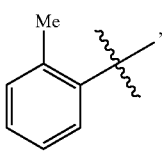

Ph(OMe) is

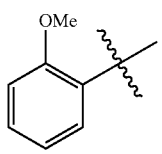 or 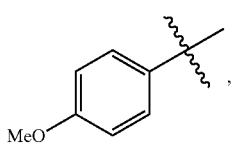

Ph(Me)₃ is

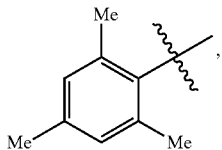

and Ph(CO₂Me) is

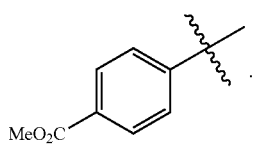

Synthesis of Ni(0) Catalysts

The synthesis of the catalysts disclosed herein follows one of the following general procedures dependent on ligand structure.

General Procedure for Ni(NHC)(Acrylate)₂ Complexes where Ortho-R₁ is not an H:

A solution of Ni(COD)₂ (1.0 equiv) and acrylate (4.0 equiv) was stirred in 4.0 mL of toluene for 30 min. In a separate vial, NHC salt (1.0 equiv) and KO-t-Bu (1.1 equiv) was stirred for 30 min in 4.0 mL of toluene. The ligand solution was added dropwise to the nickel solution, and the reaction mixture was stirred overnight at rt. The solution was filtered and the precipitate was washed with toluene. The volatiles were then removed in vacuo. Pentane was added to the resulting crude mixture, and the desired product could be precipitated at −20° C.—rt and isolated by filtration.

General Procedure for Ni(NHC)(Acrylate)₂ Complexes where Ortho-R₁ is an H:

A solution of Ni(COD)₂ (1.0 equiv) and acrylate (4.0 equiv) was stirred in 8.0 mL of toluene for 30 min. A solid mixture of NHC salt (1.0 equiv) and KO-t-Bu (1.1 equiv) was added slowly in portions over the course of 15 min. The resulting reaction mixture was stirred overnight at rt. The solution was filtered and the precipitate was washed with toluene. The volatiles were then removed in vacuo. Pentane was added to the resulting crude mixture, and the desired product could be precipitated at −20° C.—rt and isolated by filtration.

General Procedure for Ni(NHC)(Fumarate)₂ Complexes:

A THF solution of NHC (1 equiv.) was added dropwise to a solution of Ni(COD)₂ (1 equiv.) in THF at room temperature. The solution was stirred for 30 minutes and a solution of fumarate in THF (2 equiv.) was added dropwise. Afterwards, the system was stirred at room temperature for 2 h. The product could be crystallized from pentane yielding red-orange crystals.

Use of Ni(0) Catalysts

General Procedure for Air-Stability Test:

Catalyst was weighed out into a reaction vessel inside a glove box. It was then removed and exposed to air. Then the reaction vessel was pump/purged with N₂ gas three times. After purging the vessel, the general procedure for the reaction indicated was carried out.

The catalysts disclosed herein can be used for form C—C, C—N, and C—O bonds, for example, in a Suzuki coupling, a Buchwald-Hartwig coupling, or a ketone hydrosilylation.

Carbon-Nitrogen Bond Formation:

The catalyst can catalyze the reaction of (a) Ar—X or Het-X and (b) an amine, wherein Ar is aryl, Het is heteroaryl, and X is halide, sulfonate, or $C_{1-8}$alkyl-C(O)—O.

General Procedure for Ni(IPr)(Benzyl Methacrylate)$_2$ Promoted Buchwald-Hartwig Cross-Coupling:

In a glove box, catalyst Ni(IPr)(benzyl methacrylate) (2 mol %) and NaO-tBu (1.1 equiv) were dissolved in 1.0 mL of THF. Aryl halide (1.0 equiv) was added to the solution containing catalyst and NaO-tBu followed by the addition of amine (1.5 equiv). The reaction was sealed and stirred at 23° C. until no starting material remained. The reaction mixture was quenched with addition of dichloromethane and filtered through a pad of silica gel eluting with 50% v/v EtOAc/hexanes. The solvent was removed in vacuo, and the crude residue was purified via flash chromatography on silica gel to afford desired product.

Carbon-Oxygen Bond Formation:

The catalyst can catalyze the reaction of (a) Ar—X or Het-X and (b) a hydroxyl compound, wherein Ar is aryl, Het is heteroaryl, and X is halide, sulfonate, or $C_{1-8}$alkyl-C(O)—O.

Ketone Hydrosilylation

The catalyst as disclosed herein can also be used to catalyze the diastereoselective hydrosilylation of ketones which is the reaction of (a) ketone and (b) silane.

General Procedure for Ni(1,3-bis(3,5-di-tert-butylphenyl) imidazolidin-2-yl)(phenyl methacrylate)$_2$ Promoted Aldehyde Hydrosilylation:

In a glove box, Ni(1,3-bis(3,5-di-tert-butylphenyl)imidazolidin-2-yl)(phenyl methacrylate)$_2$ (2 mol %) and silane (1.1 equiv) were weighted out into a vial. A 1 mL solution of ketone (1.0 equiv) was added to the vial and it stirred at 23° C. until no starting material remained. The reaction mixture was quenched with the addition of dichloromethane and filtered through a pad of silica gel eluting with 50% v/v EtOAc/hexanes. The solvent was removed in vacuo, and the crude residue was purified via flash chromatography on silica gel to afford desired product.

Carbon-Carbon Bond Formation:

The catalyst can catalyze the reaction of (a) Ar—X or Het-X and (b) a boronic acid, boronic ester, or a trifluoroborate, wherein Ar is aryl, Het is heteroaryl, and X is halide, sulfonate, or $C_{1-8}$alkyl-C(O)—O.

General Procedure for Ni(NHC)(Acrylate)$_2$ Promoted Suzuki-Miyaura Cross-Coupling:

Ni(NHC)(acrylate)$_2$ (0.05 equiv.), $K_3PO_4$ (3 equiv.) and boronic acid (1.5 equiv) were added to a 1-dram vial with a stir bar. Then THF (0.2 M) was added followed by aryl chloride (1.0 equiv.). Reactions were quenched by a small amount of $CH_2Cl_2$ and air exposure. Reaction crude was pushed through a silica plug and yield was obtained from crude NMR using dibromomethane as an internal standard.

Aldehyde-Alkyne Reductive Coupling:

The catalyst can also catalyze the reaction of an aldehyde, alkyne and silane to produce silyl-protected allylic alcohols. In some case this reaction can be performed with high regiocontrol.

General Procedure for Aldehyde-Alkyne Reductive Coupling:

The catalyst (0.005 mmol for a 2 mol % reaction) was dissolved in 1 mL of THF, and then the alkyne (0.25 mmol), the aldehyde (0.25 mmol) and the trialkylsilane (0.50 mmol) were sequentially added to the stirred mixture. Finally, 1 mL of THF is added to achieve 0.125 M concentration and the mixture was stirred for 24 hours. The reaction was quenched opening the vial to air and 2 mL of hexane were added, stirring for 5 minutes. Finally, the crude mixture was filtered through a plug of silica eluting the product with 2% AcOEt in hexanes and product was purified by column chromatography (silica gel, hexanes).

Skipped Diene Reaction:

The catalyst can also be used to catalyze the reaction of an alkene and an alkyne. A vast array of catalytic methods have been developed for the union of two g-components via carbon-carbon bond formation. The majority of such methods involve the redistribution of atoms without a net change in the oxidation state in the components. For example, the coupling of an alkene and alkyne to produce a diene (product 1, FIG. 1), [1] the hydrovinyl of alkenes, [2] and the hydroacylation of an alkyne or alkene with an aldehyde [3] are representative examples of processes of this type. The participation of substrates lacking π-bonds in processes of this type have more recently been made possible by sequential hydrogen transfer/C—C coupling events, as illustrated by the coupling of an alcohol and allene to produce a homoallylic alcohol. [4] All of the above-mentioned processes share the characteristic of being completely atom-economical without a net formal change in oxidation state of the reactants.

A second group of processes that similarly enable the union of two π-components involves catalytic methods conducted in the presence of a reductant, wherein a net two-electron reduction of the starting components occurs during the coupling event. Examples of this type of process include the coupling of enones and alkynes to produce γ,δ-unsaturated ketones (product 2, FIG. 1), [5] the coupling of aldehydes and alkynes to produce allylic alcohols, 5 or the coupling of allylic alcohols with alkynes to produce skipped dienes. [6] Each of these processes share the characteristic of a net two-electron reduction accompanying the coupling event. In the course of exploring the development of catalytic reductive coupling methods, an unexpected conversion of enones and alkynes to skipped diene products was observed with complete deoxygenation of the enone substrate (product 3, FIG. 1).

Prior reports described the efficient reductive coupling of enals and alkynes in the presence of silane reductants and Ni(COD)$_2$ with PCy$_3$ to produce Z-enol silanes 4 (FIG. 2). [7] During efforts to extend this reactivity to enones rather than enals, exploration with a range of phosphine and N-heterocyclic carbene (NHC) ligands afforded low yields of the expected trisubstituted enol silanes, with alkyne hydrosilylation being the major side reaction. However, attempting the reaction with the unhindered NHC ligand ITol (5) while using Ti(O-i-Pr)$_4$ as a promoter for the process led to the unexpected production of skipped diene 7 in 37% isolated yield. [8] Omission of Ti(O-i-Pr)$_4$ or replacement of ITol with more common NHC ligands that bear ortho substituents on the N-aryl group such as IMes (N-mesityl) or IPr (N-[2,6-diisopropylphenyl]) failed to produce more than trace quantities of the skipped diene product 7. Replacement of Ti(O-i-Pr)4 with isopropanol [9] did result in production of 7, but in considerably lower isolated yield than when Ti(O-i-Pr)$_4$ was used.

Figure 2:
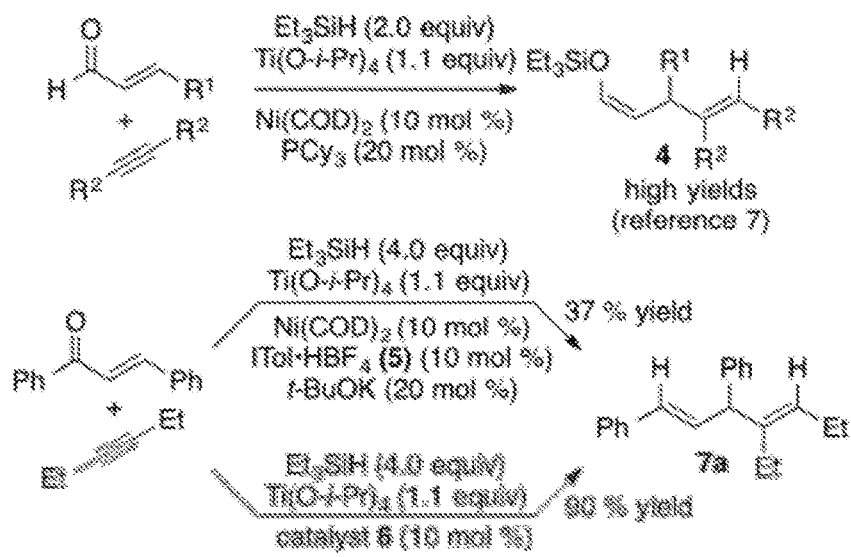
FIG. 2 shows a scheme of the reaction of an enal and an alkyne under various conditions and with different catalysts.
Figure 2:
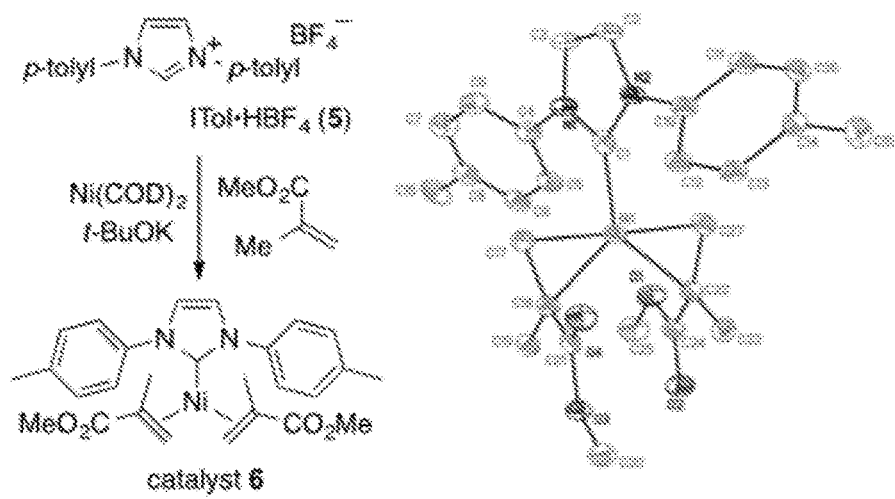

Among the many classes of NHC complexes of nickel explored in various contexts, ligands such as ITol that lack ortho substituents on the N-aryl group typically lead to low-yielding and inconsistent reactions compared with the substantially more robust analogous catalysts derived from IMes or IPr. Given this limitation and the unique behavior of ITol in promoting the formation of skipped diene 7, the preparation of stable pre-catalysts of Ni(0) coordinated with ITol was examined. [10] Among several classes of well-defined catalysts examined, Ni(0) complex 6 derived from methyl methacrylate, ITol.HBF$_4$, and Ni(COD)$_2$, had the desirable attributes of ease of preparation, moderate air stability, and high reactivity in the production of skipped dienes, as evidenced by the production of 7a in 90% isolated yield (FIG. 2). Based on this outcome, the utility of catalyst 6 was employed in further exploration of skipped dienes via the four-electron reductive coupling of enones and alkynes.

Utilizing the optimized procedure with catalyst 6, Et3SiH, and Ti(O-i-Pr)$_4$, the production of skipped diene products from a range of alkynes (2.0 equiv) with enones and enals (1.0 equiv) was examined (Table 1). Utilizing a range of enone substrates, products 7a-7h were obtained in good yield with >95:5 regioselectivity. Within these examples, the enone substrates included phenyl and methyl ketones with aromatic or aliphatic substituents at the enone β-position. The alkyne could be varied to include symmetrical or unsymmetrical alkynes including aromatic alkynes, terminal alkynes, and alkynes bearing phthalimido or silyloxy functionality. Notably, cyclic enones such as cyclohexenone (not shown) were generally ineffective substrates in this transformation. The process was very effective with enal substrates to produce products 8a-8d, including enals that possessed aromatic or aliphatic β-substituents. Notably, an enal that lacked β-substituents (product 8c) was an efficient substrate, whereas enones that lacked a β-substituent were ineffective in the transformation.

TABLE 1

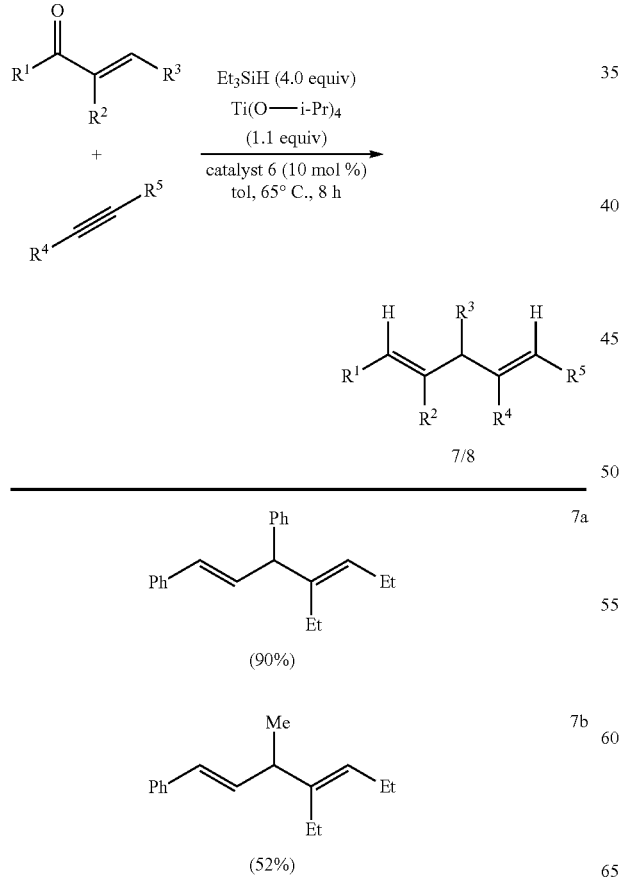

TABLE 1-continued

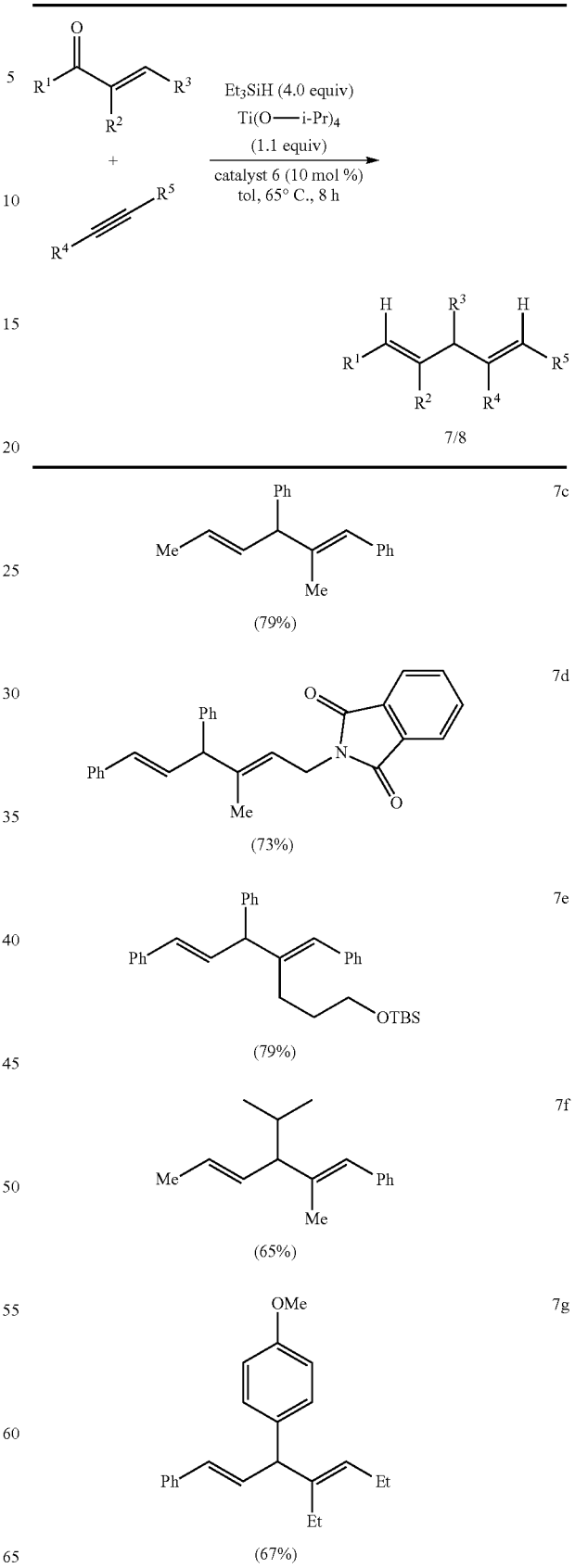

TABLE 1-continued

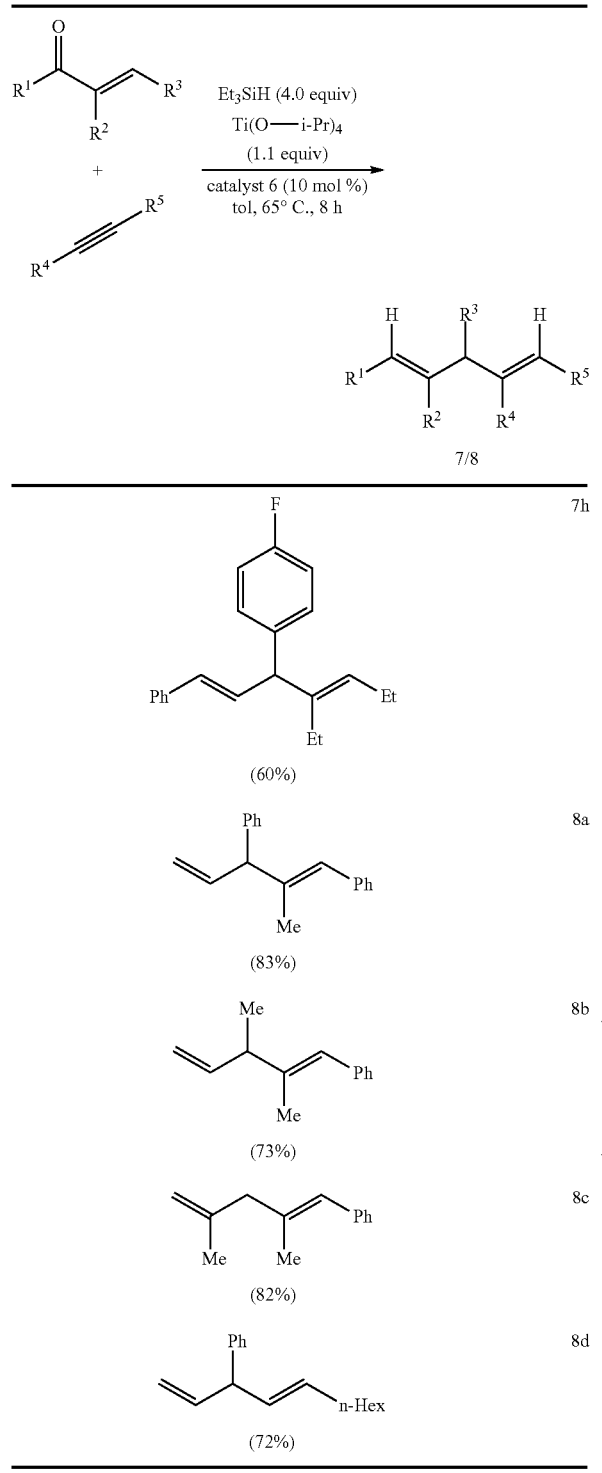

Figure 3:
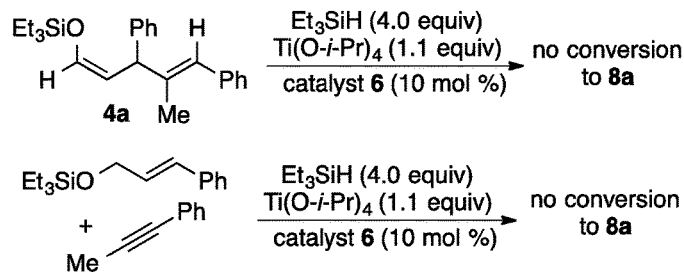
FIG. 3 shows a scheme of control reactions between a vinyl or allyl silyl ether under different conditions.

Given the novelty of the four-electron reductive coupling and the unusual combination of reactive components, a series of experiments were conducted to better understand the mechanism of this process (FIG. 3). Given the precedent for two-electron reductive couplings to generate enol silane products (i.e. product 4, FIG. 2), [7] enol silane production followed by reductive cleavage of the C—OSiEt₃ bond was the likely operative mechanistic pathway. [11] However, attempts to reduce compound 4a under the reaction conditions failed to produce skipped diene 8a. A second alternative considered was that enal 1,2-hydrosilylation was followed by alkyne addition to the resulting silylated allylic alcohol. [6] However, exposure of the silylated allylic alcohol derived from cinnamaldehyde to the reaction conditions also failed to produce skipped diene product 8a.

Figure 4:
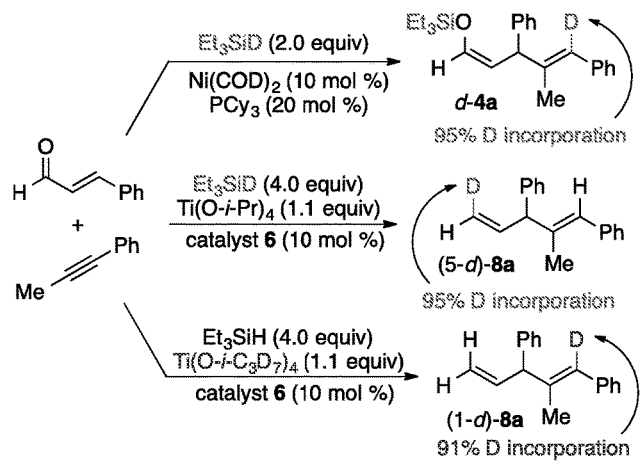
FIG. 4 shows a scheme of deuterium labeling studies investigating the mechanism of the enal-alkyne reaction.

Important insight was gained in deuterium-labelling studies in the production of d-4a and d-8a from cinnamaldehyde and phenyl propyne (FIG. 4). Using the previously published procedure with PCy$_3$ as ligand and Et$_3$SiD as reductant, 7a the deuterium label is exclusively introduced on the alkyne-derived terminus of the product d-4a as expected. However, in the skipped diene production using catalyst 6 with Et$_3$SiD, deuteration of the enal-derived terminal methylene group exclusively cis to the central carbon was observed in product (5-d)-8a, and no label incorporation in the alkyne-derived terminus was observed. Using Ti(O-i-C$_3$D$_7$)$_4$, 91% deuterium incorporation to the alkyne-derived terminus was observed in product (1-d)-8a, and no label incorporation at the enal-derived terminus was observed.

Figure 5:
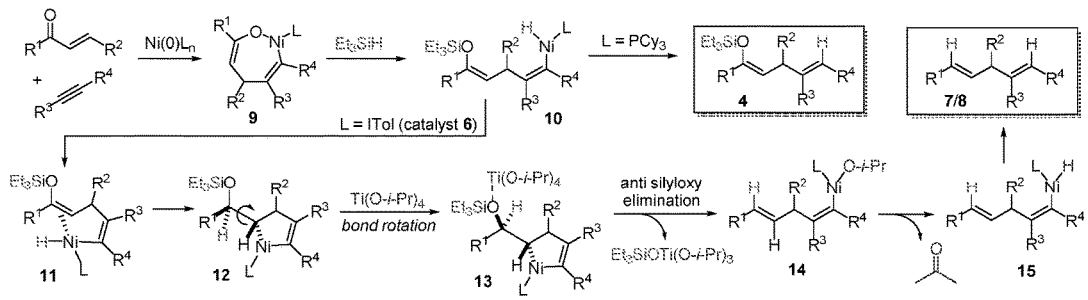
FIG. 5 shows the proposed mechanism of the enal-alkyne reaction with the Ni catalyst.

On the basis of these experiments, a mechanism that ex-plains the surprising outcome of these labeling experiments can be formulated (FIG. 5). Oxidative cyclization of the enone and alkyne with Ni(0) provides seven-membered metallacycle 9 with an r 1 nickel O-enolate motif, 12,13 and σ-bond metathesis of the silane with the Ni—O bond provides a nickel hydride intermediate 10 bearing an enol silane functionality. This intermediate serves as a common intermediate leading to two-electron or four-electron reductive coupling pathways. With PCy$_3$ as ligand, reductive elimination of the C—H bond provides the observed enol silane product 4 in analogy to previous reports. [7] However, the unique reactivity illustrated by the unhindered NHC ligand ITol likely suppresses the efficiency of reductive elimination while allowing coordination and insertion of the tethered enol silane functionality via species 11 to provide intermediate 12. Bond-rotation in 12 to produce rotamer 13 is then followed by anti-elimination of the silyloxy group, promoted by the Ti(O-i-Pr)$_4$ Lewis acid, to provide intermediate 14 with isopropoxy transfer from Ti to Ni. Extrusion of acetone [9] to generate 15 and reductive elimination of the C—H bond provides the observed product 7/8.

Several experimental observation support the above postulated mechanistic pathway. The r 1 nickel O-enolate form of metallacycle 9 (FIG. 5) is supported by the observed Z-enol silane stereochemistry of 4 and is consistent with prior crystallographic analysis of the analogous TMEDA and bipyridine metalacycles. [12] While stereoselective formation of the 1,2-trans-alkene generated by enone couplings (product 7, Table 1) could potentially be biased by the thermodynamic stability of the trans alkene, the stereochemical outcome of aldehyde coupling [product (5-d)-8a, FIG. 4] using Et$_3$SiD with catalyst 6 provides evidence for a pathway consistent with syn addition to the Z-enol silane followed by anti-silyloxy elimination. The overall positional selectivity using Et$_3$SiD and Ti(O-i-C$_3$D$_7$)$_4$ [comparing products (5-d)-8a (1-d)-8a, FIG. 4] are fully consistent with the proposed mechanistic pathway. In particular, the diverging mechanisms from intermediate 10 leading to changes in position of deuterium incorporation explain the labeling outcomes in the production of d-4a and d-8a.

EXAMPLES

General Experimental Details

Unless otherwise noted, all reactions were conducted in flame-dried or oven dried (120° C.) glassware with magnetic stirring under an atmosphere of dry nitrogen. Toluene was purified under nitrogen using a solvent purification system (Innovative Technology, Inc., Model # SPS-400-3). Benzylideneactecone (Acros), trans-chalcone (Sigma-Aldrich), (E)-1-phenylbut-2-en-1-one (AstraTech, Inc.), 1-phenyl-1-propyne (Sigma-Aldrich), 3-hexyne (Sigma-Aldrich), 1-octyne (Sigma-aldrich), and N-(2-butynyl)phthalimide (Sigma-Aldrich), and cyclohex-2-en-1-one (Sigma-Aldrich) were used as received. (E)-5-methylhex-3-en-2-one (Sigma-Aldrich), trans-cinnamaldehyde (Sigma-Aldrich), crotonaldehyde (Acros), and methacrolein (Sigma-Aldrich) were distilled prior to use. (E)-3-(4-fluorophenyl)-1-phenylprop-2-en-1-one, (E)-3-(4-methoxyphenyl)-1-phenylprop-2-en-1-one (Wong, L. Eur. J. Org. Chem. 2014, 33, 7343), tert-butyldimethyl((5-phenylpent-4-yn-1-yl)oxy)silane (Six, Y. Eur. J. Org. Chem. 2003, 7, 1157), (cinnamyloxy)triethylsilane (Ikawa, T. Tetrahedron. 2004, 60, 6901), and triethyl (((1Z,4E)-4-methyl-3,5-diphenylpenta-1,4-dien-1-yl)oxy) silane (Montgomery, J. J. Am. Chem. Soc. 2008, 130, 8132) were prepared as per the literature procedure noted. Triethylsilane (Sigma-Aldrich) was passed through basic alumina and stored under nitrogen in Schlenk glassware. Titanium (IV) isopropoxide (Sigma-Aldrich) was distilled and stored under nitrogen in Schlenk glassware. Triethylsilyldeuteride (Sigma-Aldrich) and 2-propanol-d8 (Sigma-Aldrich) were used without further purification. 1,3-Bis(4-methylphenyl) imidazolium chloride (ITol) was prepared as per the literature procedure in Arduengo, A. J., III U.S. Pat. No. 5,007, 414, 1991.

Analytical thin layer chromatography (TLC) was performed on Kieselgel 60 F254 (250 µm silica gel) glass plates and compounds were visualized with UV light and p-anisaldehyde or potassium permanganate stains. Flash column chromatography was performed using Kieselgel 60 (230-400 mesh) silica gel. Eluent mixtures are reported as v:v percentages of the minor constituent in the major constituent. All compounds purified by column chromatography were sufficiently pure for use in further experiments unless otherwise indicated.

$^1$H NMR spectra were collected at 400 MHz on a Varian MR400, at 500 MHz on a Varian Inova 500 or Varian vnmrs 500, or at 700 MHz on a Varian vnmrs 700 instrument. The proton signal of the residual, nondeuterated solvent (δ 7.26 for CHCl3 or 7.15 for C6D6) was used as the internal reference for 1H NMR spectra. 13C NMR spectra were completely heterodecoupled and measured at 125 MHz. Residual chloroform-d3 (δ 77.0) or benzene-d6 (δ 128.0) was used as an internal reference. High resolution mass spectra were recorded on a VG 70-250-s spectrometer manufactured by Micromass Corp. (Manchester UK) at the University of Michigan Mass Spectrometry Laboratory.

General Procedures

Preparation of ITol.BF$_4$

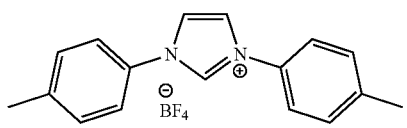

A solution of 1,3-Bis(4-methylphenyl)imidazolium chloride (5.82 g, 20.4 mmol) in 100.0 mL of water was allowed to stir. To this was added HBF$_4$ (40% in H$_2$O, 5.38 mL, 24.5 mmol) and the resulting mixture was stirred at room temperature for 12 hours. The solution was then filtered and the resulting precipitate was washed with water. The volatiles were then removed in vacuo. The resulting orange-brown solid was then recrystallized from CH$_2$Cl$_2$ and methanol to afford the desired product as a dark-brown solid (4.01 g, 0.12 mmol, 59% yield). $^1$H-NMR (500 MHz, CDCl$_3$): δ 9.36 (s, 1H), 7.69 (s, 2H), 7.58 (d, J=8.3 Hz, 4H), 7.35 (d, J=8.1 Hz, 4H), 2.40 (s, 6H). $^{13}$C-NMR (125 MHz, CDCl$_3$): δ 141.3, 132.6, 131.8, 131.1, 122.17, 122.11, 21.1. HRMS (ESI) m/z: [M-BF$_4^-$] calc. for C$_{17}$H$_{17}$N$_2^+$, 249.1386, found, 249.1387.

Preparation of Ni(ITol)(MMA)$_2$

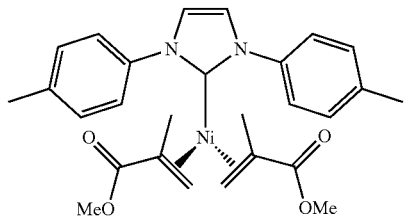

Following general procedure for Ni(0) catalyst synthesis: Ni(COD)$_2$ (550 mg, 2.00 mmol), methyl methacrylate (0.84 mL, 8.0 mmol), ITol.HBF$_4$ (672 mg, 2.00 mmol) and KO-t-Bu (246 mg, 2.20 mmol) was stirred for 30 min in 10 mL of toluene. The ligand slurry was added dropwise to the nickel solution, and the reaction mixture was stirred overnight at rt. The solution was filtered and the precipitate was washed with toluene. The volatiles were then removed in vacuo. The crude product was a dark yellow solid. Washing with pentane yielded a pale yellow powder (537 mg, 1.06 mmol, 53% yield). X-ray quality crystals were grown at −20° C. in a solution of toluene and diethyl ether. $^1$H-NMR (700 MHz, C$_6$D$_6$): The $^1$H NMR peaks reported correspond to the major isomer, although the spectrum also shows the presence of higher symmetry diastereomers. δ 7.59 (d, J=7.7 Hz, 4H), 7.03 (d, J=7.7 Hz, 4H), 6.71 (s, 2H), 3.54 (s, 6H), 3.46 (s, 2H), 2.34 (s, 2H), 2.01 (s, 6H), 1.60 (s, 6H). $^{13}$C-NMR (175 MHz, C$_6$D$_6$): Major and minor isomers are reported together. δ 174.0, 138.5, 137.6 137.5, 137.4, 129.9, 129.8, 129.6, 124.5, 123.9, 123.6, 122.0, 121.7, 121.6, 50.6, 20.9, 20.8, 20.1, 18.8. Anal calcd for C$_{27}$H$_{32}$N$_2$NiO$_4$: C (63.93%), N (5.52%), H (6.36%); found: C (63.32%), N (5.09%), H (6.52%).

Ni(IPr)(benzyl methacrylate)$_2$

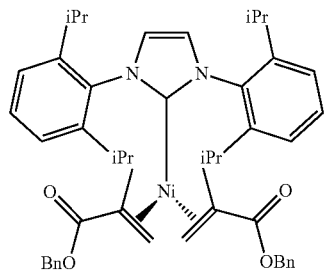

Following general procedure for Ni(0) catalyst synthesis: Ni(COD)$_2$ (138 mg, 0.5 mmol), benzyl methacrylate (0.34 mL, 2.0 mmol), IPr HCl (213 mg, 0.5 mmol) and KO-t-Bu (67.3 mg, 0.6 mmol) the desired product was precipitated from pentane at rt and was isolated as a yellow solid (395.4 mg, 99% yield).

Ni(IPr*OMe)(benzyl methacrylate)$_2$

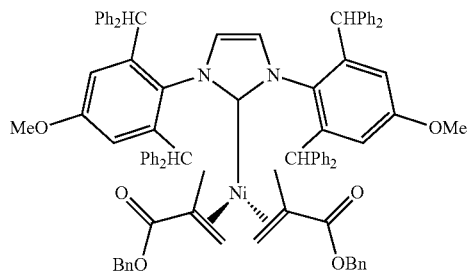

Following general procedure for Ni(0) catalyst synthesis: Ni(COD)$_2$ (138 mg, 0.5 mmol), benzyl methacrylate (0.34 mL, 2.0 mmol) and IPr*OMe (473 mg, 0.5 mmol), the desired product was precipitated from toluene and washed with pentane and was isolated as a yellow solid (579 mg, 86% yield).

Ni(1,3-bis(3,5-di-tert-butylphenyl)imidazolidin-2-yl)(phenyl methacrylate)$_2$

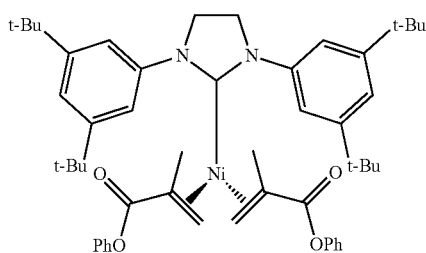

Following general procedure for Ni(0) catalyst synthesis: Ni(COD)$_2$ (257 mg, 0.9 mmol), phenyl methacrylate (0.58 mL, 3.7 mmol), 1,3-bis(3,5-di-tert-butylphenyl)imidazolinium chloride (500 mg, 0.9 mmol) and KO-t-Bu (126 mg, 1.1 mmol), the desired product was precipitated from pentane at −20° C. and was isolated as an orange solid (149 mg, 20% yield).

Ni(1,3-bis(2,4,6-trimethylphenyl)imidazolidin2-yl)(di(o-PhMe)fumarate)$_2$

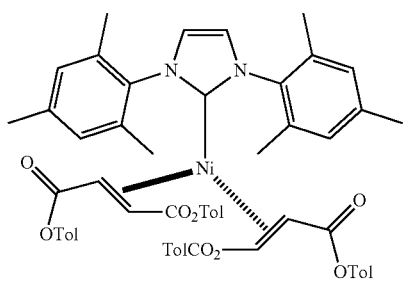

wherein Tol is

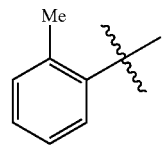 [SMILES: *c1ccccc1C]

Following general procedure for Ni (0) catalyst synthesis: Ni(COD)$_2$ (137 mg, 0.5 mmol), di(o-PhMe)fumarate (282 mg, 1.0 mmol), 1,3-bis(2,4,6-trimethylphenyl)-1,3-dihydro-2H-imidazol-2-ylidene (152 mg, 0.5 mmol), the desired product was isolated as a red crystalline solid (280 mg, 60% yield).

General Procedure for the Ni(ITol)(MMA)$_2$ Promoted Coupling of Enones or Enals and Alkynes (A)

10 mol % of Ni(ITol)(MMA)$_2$ was dissolved in 1.0 mL toluene. Enone or enal (1.0 equiv) and alkyne (2.0 equiv) were added neat to the reaction mixture. Triethylsilane (4.0 equiv) was then added, followed by addition of Ti(O-iPr)$_4$ (2.0 equiv), and the reaction mixture was placed in a heating mantle set to 65° C. and allowed to stir until starting materials were consumed (typically 8 h). The reaction mixture was then filtered through a plug of silica and was washed with a 1:1 mixture of EtOAc:hexanes. The solvent was then removed in vacuo, and the crude reaction mixture was purified via flash chromatography to afford the desired product.

((1E,4E)-4-Ethylhepta-1,4-diene-1,3-diyl)dibenzene. Table 1, Compound 7a

Following the general procedure (A), the reaction of Ni(ITol)(MMA)$_2$ (15.3 mg, 0.03 mmol), triethylsilane (139.2 mg, 1.2 mmol), titanium(IV) isopropoxide (93.7 mg, 0.33 mmol), trans-chalcone (62.4 mg, 0.3 mmol), and 3-hexyne (49.3 mg, 0.6 mmol) gave a crude residue, which was purified via flash chromatography (100% hexanes) to afford a single regioisomer in a >98:2 isolated regioselectivity (>98:2 crude regioselectivity) (74.5 mg, 0.27 mmol, 90% yield). $^1$H-NMR (500 MHz, CDCl$_3$): δ 7.39-7.21 (m, 10H), 6.51 (dd, J=15.8, 7.6 Hz, 1H), 6.28 (d, J=15.8 Hz, 1H), 5.29 (t, J=7.2 Hz, 1H), 4.21 (d, J=7.5 Hz, 1H), 2.19-2.11 (m, 3H), 1.92 (dq, J=14.6, 7.6 Hz, 1H), 1.02 (t, J=7.5 Hz, 3H), 0.96 (t, J=7.5 Hz, 3H). $^{13}$C-NMR (125 MHz, CDCl$_3$): δ 142.8, 142.2, 137.7, 132.9, 130.4, 128.9, 128.7, 128.5, 128.3, 127.0, 126.3, 126.2, 54.6, 23.3, 21.1, 14.6, 13.7. IR (film, cm$^{-1}$): 3024, 2959, 2869, 1599, 1491, 1447. HRMS (EI) m/z: [M+]$^+$ calc. for C$_{21}$H$_{24}$, 276.1878, found, 276.1866.

((1E,4E)-4-Ethyl-3-methylhepta-1,4-dien-1-yl)benzene. Table 1, Compound 7b

Following the general procedure (A), the reaction of Ni(ITol)(MMA)$_2$ (15.3 mg, 0.03 mmol), triethylsilane (139.2 mg, 1.2 mmol), titanium(IV) isopropoxide (93.7 mg, 0.33 mmol), (E)-1-phenylbut-2-en-1-one (43.8 mg, 0.3 mmol), and 3-hexyne (49.3 mg, 0.6 mmol) gave a crude residue, which was purified via flash chromatography (100% hexanes) to afford a single regioisomer in a >98:2 isolated regioselectivity (>98:2 crude regioselectivity) (34.1 mg, 0.16 mmol, 53% yield). $^1$H-NMR (400 MHz, CDCl$_3$): δ 7.33 (d, J=7.8 Hz, 2H), 7.25 (t, J=7.4 Hz, 2H), 7.17 (t, J=7.4 Hz, 1H), 6.33 (d, J=15.8 Hz, 1H), 6.13 (dd, J=15.9, 7.2 Hz, 1H), 5.17 (t, J=7.0 Hz, 1H), 2.93 (m, 1H), 2.01 (m, 4H), 1.18 (d, J=7.0 Hz, 3H), 0.96 (dt, J=2.5 7.3 Hz, 6H). $^{13}$C-NMR (125 MHz, CDCl$_3$): δ 143.7, 137.9, 135.7, 128.5, 128.1, 126.8, 126.02, 126.00, 43.2, 22.5, 21.0, 19.3, 14.7, 14.1. IR (film, cm$^{-1}$): 2963, 2870, 2164, 1497, 1458. HRMS (EI) m/z: [M+]$^+$ calc. for C$_{16}$H$_{22}$, 214.1722, found, 214.1723.

((1E,4E)-2-Methylhexa-1,4-diene-1,3-diyl)dibenzene. Table 1, Compound 7c

Following the general procedure (A), the reaction of Ni(ITol)(MMA)$_2$ (15.3 mg, 0.03 mmol), triethylsilane (139.2 mg, 1.2 mmol), titanium(IV) isopropoxide (93.7 mg, 0.33 mmol), benzylideneactecone (43.8 mg, 0.3 mmol), and 1-phenyl-1-propyne (70.2 mg, 0.6 mmol) gave a crude residue, which was purified via flash chromatography (100% hexanes) to afford a single regioisomer in a >98:2 isolated regioselectivity (>98:2 crude regioselectivity) (58.8 mg, 0.24 mmol, 79% yield). $^1$H-NMR (500 MHz, CDCl$_3$): δ 7.36-7.21 (m, 10H), 6.46 (s, 1H), 5.85 (dd, J=15.1, 7.5 Hz, 1H), 5.52 (dq, J=15.1, 7.8 Hz), 4.11 (d, J=7.8 Hz, 1H), 1.79 (s, 3H), 1.78, (s, 3H). $^{13}$C-NMR (125 MHz, CDCl$_3$): δ 142.9, 140.8, 138.4, 132.2, 129.0, 128.4, 128.3, 120.0, 127.0, 126.6, 126.3, 126.1, 57.8, 18.1, 17.3. IR (film, cm$^{-1}$): 3023, 2913, 2854, 1492, 1447. HRMS (EI) m/z: [M+]$^+$ calc. for C$_{19}$H$_{20}$, 248.1565, found, 248.1563.

2-((2E,5E)-3-Methyl-4,6-diphenylhexa-2,5-dien-1-yl)isoindoline-1,3-dione. Table 1, Compound 7d Following the general procedure (A), the reaction of Ni(ITol)(MMA)$_2$ (15.3 mg, 0.03 mmol), triethylsilane (139.2 mg, 1.2 mmol), titanium(IV) isopropoxide (93.7 mg, 0.33 mmol), trans-chalcone (62.4 mg, 0.3 mmol), and N-(2-butynyl)phthalimide (119.5 mg, 0.6 mmol) gave a crude residue, which was purified via flash chromatography (hexanes: ethyl acetate=97:3) to afford a single regioisomer in a >98:2 isolated regioselectivity (>98:2 crude regioselectivity) (93.2 mg, 0.22 mmol, 73% yield). $^1$H-NMR (500 MHz, CDCl$_3$): δ 7.86 (dd, J=5.3, 3.1 Hz, 2H), 7.21 (dd, J=5.4, 3.2 Hz, 2H), 7.35-7.20 (m, 10H), 6.45 (dd, J=15.8, 7.5 Hz, 1H), 6.31 (d, J=15.8 Hz, 1H), 5.48 (t, J=6.8 Hz, 1H), 4.40 (d, J=7.1 Hz, 2H), 4.15 (d, J=7.6 Hz, 1H), 1.82 (s, 3H). $^{13}$C-NMR (125 MHz, CDCl$_3$): δ 168.1, 141.8, 141.7, 137.3, 133.8, 132.3, 131.4, 130.9, 128.46, 128.45, 1128.40, 127.2, 126.5, 126.3, 123.2, 120.7, 57.1, 35.9, 15.9. IR (film, cm$^{-1}$): 3024, 2165, 1771, 1711 1497. HRMS (EI) m/z: [M+]$^+$ calc. for C$_{27}$H$_{23}$NO$_2$, 393.1729, found, 393.1735.

(((E)-4-((E)-Benzylidene)-5,7-diphenylhept-6-en-1-yl)oxy)(tert-butyl) dimethylsilane. Table 1, Compound 7e Following the general procedure (A), the reaction of Ni(ITol)(MMA)$_2$ (15.3 mg, 0.03 mmol), triethylsilane (139.2 mg, 1.2 mmol), titanium(IV) isopropoxide (93.7 mg, 0.33 mmol), trans-chalcone (62.4 mg, 0.3 mmol), and tert-butyldimethyl((5-phenylpent-4-yn-1-yl)oxy)silane (164.5 mg, 0.6 mmol) gave a crude residue, which was purified via flash chromatography (hexanes: ethyl acetate=99:1) to afford a single regioisomer in a >98:2 isolated regioselectivity (>98:2 crude regioselectivity) (111.0 mg, 0.24 mmol, 79% yield). $^1$H-NMR (500 MHz, CDCl$_3$): δ 7.40-7.20 (m, 15H), 6.59 (dd, J=15.9, 7.5 Hz, 1H), 6.43 (s, 1H), 6.34 (d, J=16.0, 1H), 4.39 (d, J=7.3 Hz, 1H), 3.56 (t, J=6.4 Hz, 2H), 2.46 (ddd, J=13.5, 9.4, 6.9 Hz, 1H), 2.15 (ddd, J=13.5, 9.6, 6.7 Hz, 1H), 1.83-1.65 (m, 2H), 0.93 (s, 9H), 0.09 (s, 6H). $^{13}$C-NMR (125 MHz, CDCl$_3$): δ 144.8, 142.2, 138.1, 137.4, 132.3, 131.2, 128.8, 128.7, 128.51, 128.48, 128.2, 127.9, 127.2, 126.6, 126.28, 126.27, 63.1, 55.0, 31.9, 27.6, 26.0, 18.3, −5.3. IR (film, cm$^{-1}$): 2929, 2856, 1491, 1104, 832. HRMS (EI) m/z: [M+]$^+$ calc. for C$_{32}$H$_{40}$OSi, 468.2848, found, 468.2854.

((1E,4E)-3-Isopropyl-2-methylhexa-1,4-dien-1-yl)benzene. Table 1, Compound 7f

Following the general procedure (A), the reaction of Ni(ITol)(MMA)$_2$ (15.3 mg, 0.03 mmol), triethylsilane (139.2 mg, 1.2 mmol), titanium(IV) isopropoxide (93.7 mg, 0.33 mmol), (E)-5-methylhex-3-en-2-one (33.7 mg, 0.3 mmol), and 1-phenyl-1-propyne (70.2 mg, 0.6 mmol) gave a crude residue, which was purified via flash chromatography (100% hexanes) to afford a single regioisomer in a >98:2 isolated regioselectivity (>98:2 crude regioselectivity) (41.8 mg, 0.20 mmol, 65% yield). $^1$H-NMR (400 MHz, CDCl$_3$): δ 7.33 (t, J=7.8 Hz, 2H), 7.29 (d, J=5.4 Hz, 2H), 7.19 (t, J=8.6 Hz, 1H), 6.3 (s, 1H), 5.55-5.49 (m, overlapping dd and dq, 2H), 2.36 (dd, J=8.1, 2.9 Hz, 1H), 1.84-1.77 (m, 1H), 1.82 (s, 3H), 1.72 (d, J=4.9 Hz, 3H), 0.93 (d, J=6.6 Hz, 3H), 0.90 (d, J=6.6 Hz, 3H). $^{13}$C-NMR (125 MHz, CDCl$_3$): δ 141.4, 138.6, 132.5, 128.9, 127.9, 125.8, 125.7, 125.3, 61.3, 29.6, 21.2, 20.8, 18.1, 15.3. IR (film, cm$^{-1}$): 3021, 2950, 2864, 2356, 1494, 1441. HRMS (EI) m/z: [M+]$^+$ calc. for C$_{16}$H$_{22}$, 214.1722, found, 214.1722.

1-((1E,4E)-4-Ethyl-1-phenylhepta-1,4-dien-3-yl)-4-methoxybenzene. Table 1, Compound 7g Following the general procedure (A), the reaction of Ni(ITol)(MMA)$_2$ (15.3 mg, 0.03 mmol), triethylsilane (139.2 mg, 1.2 mmol), titanium(IV) isopropoxide (93.7 mg, 0.33 mmol), (E)-3-(4-methoxyphenyl)-1-phenylprop-2-en-1-one (71.5 mg, 0.3 mmol), and 3-hexyne (49.3 mg, 0.6 mmol) gave a crude residue, which was purified via flash chromatography (hexanes: ethyl acetate=99:1) to afford a single regioisomer in a >98:2 isolated regioselectivity (>98:2 crude regioselectivity) (59.7 mg, 0.20 mmol, 65% yield). $^1$H-NMR (500 MHz, CDCl$_3$): δ 7.37 (d, J=7.3 Hz, 2H), 7.30 (t, J=7.6 Hz, 2H), 7.21 (t, J=7.1 Hz, 1H), 7.17 (d, J=8.5 Hz, 2H), 6.87 (d, J=8.5, 2H), 6.47 (dd, J=15.9, 7.6 Hz, 1H), 6.23 (d, J=15.8 Hz, 1H), 5.26 (t, J=7.3, 1H), 4.15 (d, J=7.6 Hz, 1H), 3.82 (s, 3H), 2.16-2.10 (m, 3H), 1.93-1.89 (m, 1H), 1.01 (t, J=7.3 Hz, 3H), 0.95 (t, J=7.3 Hz, 3H). $^{13}$C-NMR (125 MHz, CDCl$_3$): δ 158.1, 142.5, 137.7, 134.8, 133.2, 130.1, 129.6, 128.7, 128.4, 127.0, 126.2, 113.6, 55.2, 53.7, 23.2, 21.1, 14.6, 13.7. IR (film, cm$^{-1}$): 2960, 2869, 2054, 1507, 1459. HRMS (EI) m/z: [M+]$^+$ calc. for C$_{22}$H$_{26}$O, 306.1984, found, 306.1985.

1-((1E,4E)-4-Ethyl-1-phenylhepta-1,4-dien-3-yl)-4-fluorobenzene Table 1, Compound 7h Following the general procedure (A), the reaction of Ni(ITol)(MMA)$_2$ (15.3 mg, 0.03 mmol), triethylsilane (139.2 mg, 1.2 mmol), titanium(IV) isopropoxide (93.7 mg, 0.33 mmol), (E)-3-(4-fluorophenyl)-1-phenylprop-2-en-1-one (67.9 mg, 0.3 mmol), and 3-hexyne (49.3 mg, 0.6 mmol) gave a crude residue, which was purified via flash chromatography (hexanes: ethyl acetate=99:1) to afford a single regioisomer in a >98:2 isolated regioselectivity (>98:2 crude regioselectivity) (53.0 mg, 0.18 mmol, 60% yield). $^1$H-NMR (500 MHz, CDCl$_3$): δ 7.36 (d, J=7.3 Hz, 2H), 7.31 (t, J=7.6 Hz, 2H), 7.20 (m, overlapping t and t, 3H), 7.01 (t, J=8.8 Hz, 2H), 6.45, (dd, J=15.8, 7.6 Hz, 1H), 6.22 (d, J=15.8 Hz, 1H), 5.26 (t, J=7.1 Hz, 1H), 4.18 (d, J=7.3 Hz, 1H), 2.15-2.10 (m, 3H), 1.90 (m, 1H), 1.01 (t, J=7.6 Hz, 3H), 0.95 (t, J=7.8 Hz, 3H). $^{13}$C-NMR (125 MHz, CDCl$_3$): δ 161.5 (d, J=244.1 Hz), 142.1, 138.3 (d, J=2.8 Hz), 137.5, 132.6, 130.6, 130.1 (d, J=7.6 Hz), 129.1, 128.5, 127.1, 126.2, 115.1 (d, J=21 Hz), 53.7, 23.2, 21.1, 14.6, 13.7. A $^{13}$C spectrum was also acquired at 100 MHz (CDCl$_3$) in order to elucidate the fluorine coupling assignments. IR (film, cm$^{-1}$): 3022, 2960, 2869, 1505, 1448. HRMS (EI) m/z: [M+]$^+$ calc. for C$_{21}$H$_{23}$F, 294.1784, found, 294.1776.

(E)-(2-Methylpenta-1,4-diene-1,3-diyl)dibenzene. Table 1, Compound 8a

Following the general procedure (A), the reaction of Ni(ITol)(MMA)$_2$ (15.3 mg, 0.03 mmol), triethylsilane (139.2 mg, 1.2 mmol), titanium(IV) isopropoxide (93.7 mg, 0.33 mmol), trans-cinnamaldehyde (39.7 mg, 0.3 mmol), and 1-phenyl-1-propyne (70.2 mg, 0.6 mmol) gave a crude residue, which was purified via flash chromatography (100% hexanes) to afford a single regioisomer in a >98:2 isolated regioselectivity (>98:2 crude regioselectivity) (51.3 mg, 0.22 mmol, 73% yield). $^1$H-NMR (500 MHz, CDCl$_3$): δ 7.36-7.22 (m, 10H), 6.46 (s, 1H), 6.24 (ddd, J=17.3, 10.2, 7.3 Hz, 1H), 5.24 (d, J=10.2 Hz, 1H), 5.08 (d, J=17.2 Hz, 1H), 4.17 (d, J=7.3 Hz, 1H), 1.80 (s, 3H). $^{13}$C-NMR (125 MHz, CDCl$_3$): δ 141.9, 140.0, 139.5, 138.3, 129.0, 128.5, 128.4, 128.08, 128.04, 127.8, 127.0, 126.4, 126.2, 116.4, 58.7, 17.4. IR (film, cm$^{-1}$): 3023, 2193, 2049, 1494, 1332. HRMS (EI) m/z: [M+]$^+$ calc. for C$_{18}$H$_{18}$, 234.1409, found, 234.1405.

(E)-(2,3-Dimethylpenta-1,4-dien-1-yl)benzene. Table 1, Compound 8b

Following the general procedure (A), the reaction of Ni(ITol)(MMA)$_2$ (15.3 mg, 0.03 mmol), triethylsilane (139.2 mg, 1.2 mmol), titanium(IV) isopropoxide (93.7 mg, 0.33 mmol), crotonaldehyde (39.7 mg, 0.3 mmol), and 1-phenyl-1-propyne (70.2 mg, 0.6 mmol) gave a crude residue, which was purified via flash chromatography (100% hexanes) to afford a single regioisomer in a >98:2 isolated regioselectivity (>98:2 crude regioselectivity) (37.7 mg, 0.22 mmol, 73% yield). $^1$H-NMR (500 MHz, CDCl$_3$): δ 7.34 (t, J=7.6 Hz, 2H), 7.28 (d, J=6.8 Hz, 2H), 7.21 (t, 7.3 Hz, 1H), 6.37 (s, 1H), 5.92 (ddd, J=17.0, 10.3, 6.5 Hz, 1H), 5.13-5.07 (m, 2H), 3.09-2.88 (m, 1H), 1.84 (s, 3H), 1.26 (d, J=7.1, 3H). $^{13}$C-NMR (125 MHz, CDCl$_3$): δ 142.2, 141.8, 138.5, 128.9, 128.0, 125.9, 124.5, 113.6, 46.8, 18.1, 15.7. IR (film, cm$^{-1}$): 2962, 2175, 2016, 1278, 1027. HRMS (EI) m/z: [M+]$^+$ calc. for C$_{13}$H$_{16}$, 172.1252, found, 172.1246.

(E)-(2,4-dimethylpenta-1,4-dien-1-yl)benzene. Table 1, Compound 8c

Following the general procedure (A), the reaction of Ni(ITol)(mma)$_2$ (15.3 mg, 0.03 mmol), triethylsilane (139.2 mg, 1.2 mmol), titanium(IV) isopropoxide (93.7 mg, 0.33 mmol), methacrolein (39.7 mg, 0.3 mmol), and 1-phenyl-1-propyne (70.2 mg, 0.6 mmol) gave a crude residue, which was purified via flash chromatography (100% hexanes) to afford a single regioisomer in a >98:2 isolated regioselectivity (>98:2 crude regioselectivity) (42.3 mg, 0.25 mmol, 82% yield). $^1$H-NMR (500 MHz, CDCl$_3$): δ 7.35 (t, J=7.6 Hz, 2H), 7.30 (d, J=7.6 Hz, 2H), 7.22 (t, J=7.3 Hz, 1H), 6.36 (s, 1H), 4.88 (s, 1H), 4.84 (s, 1H), 2.90 (s, 2H), 1.85 (s, 3H), 1.76 (s, 3H). $^{13}$C-NMR (125 MHz, CDCl$_3$): δ 143.7, 138.5, 136.7, 128.8, 128.1, 126.8, 126.0, 112.3, 49.6, 21.9, 17.3. IR (film, cm$^{-1}$): 3072, 2970, 2909, 2163, 1497. HRMS (EI) m/z: [M+]$^+$ calc. for C$_{13}$H$_{16}$, 172.1252, found, 172.1245.

(E)-Undeca-1,4-dien-3-ylbenzene. Table 1, Compound 8d

Following the general procedure (A), the reaction of Ni(ITol)(MMA)$_2$ (15.3 mg, 0.03 mmol), triethylsilane (139.2 mg, 1.2 mmol), titanium(IV) isopropoxide (93.7 mg, 0.33 mmol), trans-cinnamaldehyde (39.7 mg, 0.3 mmol), and 1-octyne (66.1 mg, 0.6 mmol) gave a crude residue, which was purified via flash chromatography (100% hexanes) to afford a single regioisomer in a >98:2 isolated regioselectivity (>98:2 crude regioselectivity) (49.3 mg, 0.22 mmol, 72% yield). The spectral data matches that previously reported in the literature (Table VII, Compound 16 in *J. Org. Chem.* 1980, 45, 1640). $^1$H-NMR (500 MHz, CDCl$_3$): δ 7.31 (dt, J=8.1 Hz, 1.7 Hz, 2H), 7.22-7.19 (m, 3H), 6.02 (ddd, J=17.0, 10.2, 6.8 Hz, 1H), 5.61 (dd, J=15.3, 7.0 Hz, 1H), 5.51-5.46 (ddt, 15.4, 6.7, 0.8 Hz, 1H), 5.10 (ddd, J=10.2, 1.4, 1.4 Hz, 1H), 5.04 (ddd, J=17.1, 1.4, 1.4 Hz, 1H), 4.01 (dd, J=7.0, 6.9 Hz, 1H), 2.04 (dt, J=7.1, 7.0 Hz, 2H), 1.39-1.24 (m, 8H), 0.88 (t, 7.1 Hz, 3H). $^{13}$C-NMR (125 MHz, CDCl$_3$): δ 143.4, 140.9, 131.8, 131.4, 128.4, 127.9, 126.2, 114.8, 52.2, 32.6, 31.7, 29.3, 28.9, 22.6, 14.1. IR (film, cm$^{-1}$): 3025, 2956, 2924, 2854, 2036, 1495. HRMS (EI) m/z: [M+]$^+$ calc. for C$_{17}$H$_{24}$, 228.1878, found, 228.1884.

Deuterium Labeling Studies triethyl(((1Z,4E)-4-methyl-3,5-diphenylpenta-1,4-dien-1-yl-5-d)oxy)silane. Entry d-4a Following a previously published modified procedure from Montgomery, J. Am. Chem. Soc. 2008, 130, 8132, utilizing triethyl(silane-d), a crude residue was obtained, which was purified via flash chromatography (100% hexanes) to afford a single regioisomer in a >98:2 isolated regioselectivity (>98:2 crude regioselectivity) with >95% deuterium incorporation at the proton shown above (36.1 mg, 0.10 mmol, 33% yield). The undeuterated standard was previously reported (Table 2, entry 3 of *J. Am. Chem. Soc.* 2008, 130, 8132.) $^1$H-NMR (400 MHz, CDCl$_3$): δ 7.34-7.18 (m, 10H), 6.40 (d, J=5.6 Hz, 1H), 4.88 (dd, J=5.6, 9.6 Hz, 1H), 4.75 (d, J=9.6 Hz, 1H), 1.78 (d, J=1.2 Hz, 3H), 0.99 (t, J=8.0 Hz, 9H), 0.67 (q, J=8.0 Hz, 6H).

((1E,4Z)-2-methylpenta-1,4-diene-1,3-diyl-5-d) dibenzene. Entry (5-d)-8a

Following the general procedure (A), the reaction of Ni(ITol)(MMA)$_2$ (15.3 mg, 0.03 mmol), triethyl(silane-d) (140.2 mg, 1.2 mmol), titanium(IV) isopropoxide (93.7 mg, 0.33 mmol), trans-cinnamaldehyde (39.7 mg, 0.3 mmol), and 1-phenyl-1-propyne (70.2 mg, 0.6 mmol) gave a crude residue, which was purified via flash chromatography (100% hexanes) to afford a single regioisomer in a >98:2 isolated regioselectivity (>98:2 crude regioselectivity) with >95% deuterium incorporation at the proton shown above (51.3 mg, 0.22 mmol, 63% yield). $^1$H-NMR (500 MHz, CDCl$_3$): δ 7.36-7.21 (m, 10H), 6.46 (s, 1H), 6.22 (m, 1H), 5.21 (d, J=10.2 Hz, 1H), 4.16 (d, J=7.1 Hz, 1H), 1.80 (s, 3H). $^{13}$C-NMR (125 MHz, CDCl$_3$): δ 141.9, 140.0, 139.4, 138.3, 128.4, 128.5, 128.4, 128.0, 127.0, 126.4, 126.2, 116.1 (t, J=23.8 Hz), 58.6, 17.4.

tetrakis((propan-2-yl-d$_7$)oxy)titanium

Titanium(IV) isopropoxide (1.0 ml, 3.4 mmol) was added to a flame dried round bottom under a nitrogen atmosphere. To this was added 2-propanol-ds (99.5%) (2.0 ml, 26.1 mmol) and the mixture was allowed to stir for 2 h. The reaction mixture was then concentrated, and the addition of 2-propanol-ds (99.5%) (2.0 ml, 26.1 mmol) and subsequent concentration after stirring for two hours was repeated two more times to afford the desired product with 99% deuterium incorporation. Standard Titanium(IV) isopropoxide, MS (EI) m/z: [M-CH$_3$]$^+$ calc. for C$_{12}$H$_{28}$O$_4$Ti, 269.12, found, 269.1. Titanium(IV) isopropoxide-d$_{28}$ MS (EI) m/z: [M-CD$_3$]$^+$ calc. for C$_{12}$D$_{28}$O$_4$Ti, 294.28, found, 294.3. No d$_{21}$, d$_{14}$, or d$_7$ products detected. Characteristic peaks at m/z 290.3, 287.2, 283.2, 280.2, 276.2, and 273.1 indicate incomplete deuterium incorporation.

(E)-(2-methylpenta-1,4-diene-1,3-diyl-1-d)dibenzene. Entry (1-d)-8a

Following the general procedure (A), the reaction of Ni(ITol)(MMA)$_2$ (15.3 mg, 0.03 mmol), triethylsilane (140.2 mg, 1.2 mmol), titanium(IV) isopropoxide-d$_{28}$ (99%) (93.7 mg, 0.33 mmol), trans-cinnamaldehyde (39.7 mg, 0.3 mmol), and 1-phenyl-1-propyne (70.2 mg, 0.6 mmol) gave a crude residue, which was purified via flash chromatography (100% hexanes) to afford a single regioisomer in a >98:2 isolated regioselectivity (>98:2 crude regioselectivity) with 91% deuterium incorporation at the proton shown above (35.6 mg, 0.15 mmol, 51% yield). $^1$H-NMR (500 MHz, CDCl$_3$): δ 7.36-7.22 (m, 10H), 6.46 (s, 0.09H), 6.24 (ddd, J=17.3, 10.2, 7.3 Hz, 1H), 5.24 (d, J=10.2 Hz, 1H), 5.08 (d, J=17.2 Hz, 1H), 4.17 (d, J=7.3 Hz, 1H), 1.80 (s, 3H). $^{13}$C-NMR (125 MHz, CDCl$_3$): δ 141.9, 140.0, 139.5, 138.2, 128.9, 128.5, 128.4, 128.1, 128.0, 127.8, 127.0, 126.4, 126.2, 116.3, 58.7, 17.3.

2,6-dimethyl-N-phenylaniline

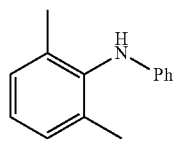

Following the general procedure for Buchwald-Hartwig cross-coupling: Ni(IPr*$^{OMe}$)(benzyl methacrylate) (5.0 mg, 0.004 mmol), NaO-tBu (23 mg, 0.24 mmol), 2-chloro-1,3-dimethylbenzene (28 mg, 0.2 mmol) and aniline (28 mg, 0.3 mmol) were stirred for 24 h at 50° C. yield obtained from crude NMR using dibromomethane as an internal standard (99% yield).

2,4,6-trimethyl-N-(o-tolyl)aniline

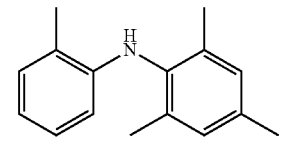 [SMILES: Cc1cc(C)c(Nc2ccccc2C)c(C)c1]

Following the general procedure for Buchwald-Hartwig cross-coupling: Ni(IPr*$^{OMe}$)(benzyl methacrylate) (5.0 mg, 0.004 mmol), NaO-tBu (23 mg, 0.24 mmol), 2-chlorotoluene (25 mg, 0.2 mmol) and 2,4,6-trimethylaniline (41 mg, 0.3 mmol) were stirred for 16 h at 23° C. yield obtained from crude NMR using dibromomethane as an internal standard (76% yield).

4-(4-(trifluoromethyl)phenyl)morpholino

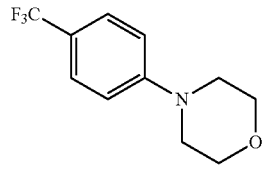

Following the general procedure for Buchwald-Hartwig cross-coupling: Ni(IPr)(benzyl methacrylate) (8.0 mg, 0.01 mmol), NaO-tBu (58 mg, 0.6 mmol), 1-chloro-4-(trifluoromethyl)benzene (67 μL, 0.5 mmol) and morpholine (66 μL, 0.75 mmol) stirred for 15 hr followed by column chromatography (109 mg, 95% yield).

Following general procedure for air stability test, Ni(IPr)(benzyl methacrylate) (8.0 mg, 0.01 mmol), NaO-tBu (58 mg, 0.6 mmol), 1-chloro-4-(trifluoromethyl)benzene (67 μL, 0.5 mmol) and morpholine (66 μL, 0.75 mmol) stirred for 15 hr followed by column chromatography (98.2 mg, 85% yield).

((((1R,2S,5R)-2-isopropyl-5-methylcyclohexyl)oxy)triphenylsilane

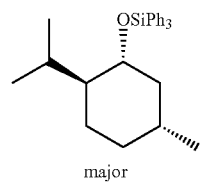

major

Following general procedure for aldehyde hydrosilylation, Ni(1,3-bis(3,5-di-tert-butylphenyl)imidazolidin-2-yl)(phenyl methacrylate)$_2$ (8.3 mg, 0.01 mmol), Ph$_3$SiH (156 mg, 0.6 mmol), and (−) menthone (77 mg, 0.5 mmol) stirred for 6 hr and produced a crude residue that could be purified by column chromatography on silica gel (201 mg, dr=5:1, 97% yield)

Following general procedure for air stability test followed by the general procedure for aldehyde hydrosilylation: Ni(1,3-bis(3,5-di-tert-butylphenyl)imidazolidin-2-yl)(phenyl methacrylate)$_2$ (8.3 mg, 0.01 mmol), Ph$_3$SiH (156 mg, 0.6 mmol), and (−) menthone (77 mg, 0.5 mmol) stirred for 6 hr and produced a crude residue that could be purified by column chromatography on silica gel (203 mg, dr=5:1, 98% yield)

5-ene-17-(triphenylsilyloxy)-3β-andostranol

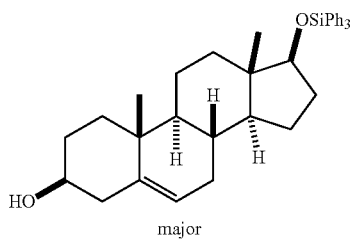

major

Following general procedure for air stability test followed by the general procedure for aldehyde hydrosilylation: Ni(1,3-bis(3,5-di-tert-butylphenyl)imidazolidin-2-yl)(phenyl methacrylate)$_2$ (8.3 mg, 0.01 mmol), Ph$_3$SiH (156 mg, 0.6 mmol), and trans-dehydroandrosterone (144.2 mg, 0.5 mmol) stirred for 6 hr and produced a crude residue that could be purified by column chromatography on silica gel (258 mg, dr=4:1, 94% yield)

Triphenyl(1,3,3-trimethylbicyclo[2.2.1]heptan-2-yloxy)silane

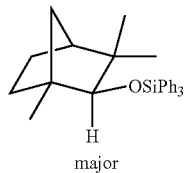

major

Following general procedure for air stability test followed by the general procedure for aldehyde hydrosilylation: Ni(1,3-bis(3,5-di-tert-butylphenyl)imidazolidin-2-yl)(phenyl methacrylate)$_2$ (8.3 mg, 0.01 mmol), Ph$_3$SiH (156 mg, 0.6 mmol), and (1R)-(−)-Fenchone (80.3 μL, 0.5 mmol) stirred for 6 hr and produced a crude residue that could be purified by column chromatography on silica gel (204 mg, dr=15:1, 99% yield.

(E)-triethyl((2-methyl-1,3-diphenylallyl)oxy) silane

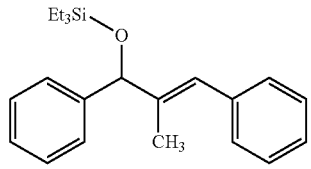

Following general procedure for aldehyde-alkyne reductive coupling, Ni(IMes)(di(o-PhMe) fumarate)$_2$ (3.7 mg, 0.0 mmol), benzaldehyde (21 mg, 0.2 mmol), 1-phenyl propyne (23.2 mg, 0.2 mmol) and triethylsilane (46.5 mg, 0.4 mmol). Product could be purified by column chromatography on silica gel using pure hexanes (58 mg, 98:2, 85% yield).

4-(trifluoromethyl)-1,1'-biphenyl

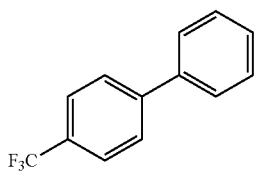 [SMILES: FC(F)(F)c1ccc(-c2ccccc2)cc1]

Following general procedure for Suzuki-Miyaura cross couplings: Ni(ITol)(methyl methacrylate)$_2$ (2.5 mg, 0.005 mmol), K$_3$PO$_4$ (64 mg, 0.3 mmol), phenyl boronic acid (18 mg, 0.15 mmol), 4-chlorobenzotrifluoride (18 mg, 0.1 mmol). The reaction was stirred for 16 h at 23° C. (63% yield).

Following general procedure for Suzuki-Miyaura cross couplings: Ni(SIPr)(benzyl methacrylate)$_2$ (4.0 mg, 0.005 mmol), K$_3$PO$_4$ (64 mg, 0.3 mmol), phenyl boronic acid (18 mg, 0.15 mmol), 4-chlorobenzotrifluoride (18 mg, 0.1 mmol). The reaction was stirred for 16 h at 23° C. (90% yield).

2-methyl-1,1'-biphenyl

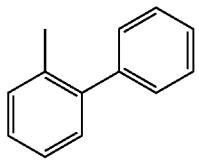

Following general procedure for Suzuki-Miyaura cross couplings: Ni(ITol)(methyl methacrylate)$_2$ (2.5 mg, 0.005 mmol), K$_3$PO$_4$ (64 mg, 0.3 mmol), phenyl boronic acid (18 mg, 0.15 mmol), 2-chlorotoluene (13 mg, 0.1 mmol). The reaction was stirred for 4 h at 80° C. (31% yield).

REFERENCES (1) (a) Trost, et al. Angew. Chem. Int. Ed. 2005, 44, 6630-6666. (b) Trost, et al. Synlett. 1998, 1-16. (c) Trost, et al. J. Am. Chem. Soc. 2005, 127, 17921-17937. (d) Trost, et al. J. Am. Chem. Soc. 1999, 121, 9728-9729. (e) Trost, et al. J. Am. Chem. Soc. 2002, 124, 5025-5036.

(2) (a) Hoshimoto, et al. Acc. Chem. Res. 2015, 48, 1746-1755. (b) Hoshimoto, et al. Angew. Chem. Int. Ed. 2012, 51, 10812-10815. (c) Chen, et al. J. Am. Chem. Soc. 2015, 137, 3157-3160. (d) Chen, et al. J. Am. Chem. Soc. 2014, 136, 3772-3775. (e) Kou, et al. J. Am. Chem. Soc. 2014, 136, 9471-9476. (f) Prades, et al. Angew. Chem. Int. Ed. 2015, 54, 8520-8524. (g) Castaing, et al. Angew. Chem.—Int. Edit. 2013, 52, 13280-13283. (h) Chaplin, et al. J. Am. Chem. Soc. 2012, 134, 4885-4897. (i) Yang, et al. ACS Catal. 2015, 5, 3054-3057.

(3) (a) RajanBabu. Chem. Rev. 2003, 103, 2845-2860. (b) RajanBabu. Synlett 2009, 853-885. (c) Mans, et al. J. Am. Chem. Soc. 2011, 133, 5776-5779. (d) Zhang, et al. J. Am. Chem. Soc. 2006, 128, 5620-5621. (e) Ho, et al. Angew.

Chem. Int. Ed. 2010, 49, 9182-9186. (f) Ho, et al. Angew. Chem. Int. Ed. 2015, 54, 4512-4516.

(4) (a) Bower, et al. Angew. Chem., Int. Ed. 2009, 48, 34-46. (b) Patman, et al. J. Am. Chem. Soc. 2009, 131, 2066-2067. (c) Bower, et al. J. Am. Chem. Soc. 2007, 129, 15134-15135. (d) Gao, et al. J. Am. Chem. Soc. 2013, 135, 4223-4226. (e) Herath, et al. J. Am. Chem. Soc. 2008, 130, 469-471.

(5) (a) Montgomery. "Organonickel Chemistry" in Organometallics in Synthesis: Fourth Manual Lipshutz, B. H. (Ed.) Wiley, Hoboken, N.J. 2013, pp. 319-428. (b) Jackson, et al. Acc. Chem. Res. 2015, 48, 1736-1745. (c) Montgomery. Angew. Chem. Int. Ed. 2004, 43, 3890-3908. (d) Montgomery, et al. In Metal Catalyzed Reductive C—C Bond Formation: A Departure from Preformed Organometallic Reagents 2007; Vol. 279, p 1-23. (e) Moslin, et al. Chem. Commun. 2007, 4441-4449. (f) Standley, et al. Acc. Chem. Res. 2015, 48, 1503-1514. (g) Ikeda. Angew. Chem. Int. Ed. 2003, 42, 5120-5122. (h) Skukcas, et al. Acc. Chem. Res. 2007, 40, 1394-1401. (i) Jang, et al. Acc. Chem. Res. 2004, 37, 653-661. (j) Ngai, et al. J. Org. Chem. 2007, 72, 1063-1072. (k) Jeganmohan, et al. Chem. Eur. J. 2008, 14, 10876-10886. (l) Gandeepan, et al. Acc. Chem. Res. 2015, 48, 1194-1206.

(6) (a) Kolundzic, et al. J. Am. Chem. Soc. 2007, 129, 15112-15113. (b) Lysenko, et al. J. Am. Chem. Soc. 2008, 130, 15997-16002. (c) Jeso, et al. J. Am. Chem. Soc. 2010, 132, 11422-11424. (d) Macklin, et al. Nat. Chem. 2010, 2, 638-643. (e) Das, et al. Angew. Chem. Int. Ed. 2011, 50, 9459-9461.

(7) (a) Herath, et al. J. Am. Chem. Soc. 2008, 130, 8132-8133. (b) Li, et al. J. Am. Chem. Soc. 2009, 131, 17024-17029.

(8) For representative other approaches to skipped dienes, see references 1 and 6 and the following: (a) Sharma, et al. J. Am. Chem. Soc. 2010, 132, 3295-3297. (b) Qian, et al. Chem. Commun. 2013, 49, 9839-9841. (c) Braddock, et al. Synlett 2001, 1909-1912. (d) Thadani, et al. Org. Lett. 2002, 4, 4317-4320.

(9) (a) Ohashi, et al. J. Am. Chem. Soc. 2011, 133, 14900-14903. (b) Beaver, et al. Org. Lett. 2011, 13, 4140-4143. (c) Nakai, et al. J. Am. Chem. Soc. 2014, 136, 7797-7800.

(10) (a) Arduengo, et al. J. Am. Chem. Soc. 1992, 114, 5530-5534. (b) Haynes, et al. "Nickel Complexes of N-Heterocyclic Carbenes" in N-Heterocyclic Carbenes: Effective Tools for Organometallic Synthesis Nolan, S. P. (Ed.) Wiley-VCH 2014, 371-396. (c) Clement, et al. Organometallics 2006, 25, 4155-4165. (d) Iglesias, et al. Organometallics 2012, 31, 6312-6316. (d) Jarvis, et al. J. C. S., Dalton Trans. 1995, 2033-2040.

(11) (a) Alvarez-Bercedo, et al. J. Am. Chem. Soc. 2010, 132, 17352-17353. (b) Cornella, et al. J. Am. Chem. Soc. 2013, 135, 1997-2009. (c) Sergeev, et al. Science 2011, 332, 439-443. (d) Kelley, et al. J. Am. Chem. Soc. 2012, 134, 5480-5483. (e) Tobisu, et al. Chem. Sci. 2015, 6, 3410-3414.

(12) (a) Amarasinghe, et al. Organometallics 2001, 20, 370-372. (b) Mahandru, et al. J. Am. Chem. Soc. 2003, 125, 13481-13485.

(13) For 13 nickel enolates with the opposite C=C stereochemistry: (a) Ho, et al. Angew. Chem. Int. Ed. 2008, 47, 1893. (b) Tamaki, et al. Chem. Eur. J. 2009, 15, 10083. (c) Campora, et al. J. Am. Chem. Soc. 2003, 125, 1482.

What is claimed is:

1. A catalyst having a structure of formula (I) or (II):

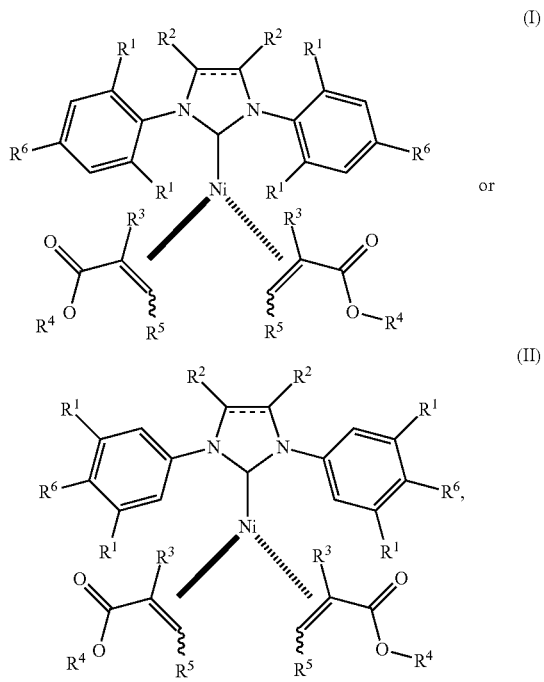

wherein
the dashed line is an optional double bond;
each $R^1$ is independently selected from the group consisting of H, $C_{1-8}$alkyl and $C_{1-2}$alkylenearyl;
each $R^2$ is independently selected from the group consisting of H, halo, $C_{1-3}$alkyl, and aryl, or both $R^2$ together with the carbons to which they are attached form a 6-membered ring;
each $R^3$ is the same and is H, $C_{1-4}$alkyl, or aryl;
each $R^4$ is the same and is $C_{1-6}$alkyl, $C_{0-2}$alkylene-aryl or $C_{0-2}$alkylene-$C_{2-8}$alkene;
each $R^5$ is the same and is H, $C_{1-6}$alkyl, aryl, $CO_2C_{0-2}$alkylene-aryl, $CO_2C_{0-2}$alkylene-$C_{2-8}$alkene, $CO_2iPr$ or $CO_2tBu$; and
each $R^6$ is the same and is H, $C_{1-6}$alkyl, $C_{1-6}$alkoxy, or O-aryl, with the proviso that at least one of $R^1$ and $R^6$ is not H.

2. The catalyst of claim 1, wherein the dashed line represents a double bond.

3. The catalyst of claim 1, wherein each $R^1$ is the same.

4. The catalyst of claim 1, wherein $R^1$ is selected from the group consisting of methyl, ethyl, propyl, isopropyl, butyl, sec-butyl, isobutyl, t-butyl, pentyl, 3-pentyl, and diphenylmethyl.

5. The catalyst of claim 1, wherein each $R^2$ is selected from H, chloro, and methyl, or wherein both $R^2$ together with the carbons to which they are attached form a 6-membered ring.

6. The catalyst of claim 1, wherein $R^3$ is aryl.

7. The catalyst of claim 1, wherein $R^3$ is $C_{1-4}$alkyl or H.

8. The catalyst of claim 1, wherein $R^4$ is $C_{0-2}$alkylene-aryl.

9. The catalyst of claim 1, wherein $R^4$ is $C_{0-2}$alkylene-$C_{2-8}$alkene.

10. The catalyst of claim 1, wherein $R^4$ is $C_{2-6}$alkyl.

11. The catalyst of claim 1, wherein $R^5$ is H.

12. The catalyst of claim 1, wherein $R^5$ is $C_{1-6}$alkyl.

13. The catalyst of claim 1, wherein $R^5$ is aryl.

14. The catalyst of claim 1, wherein $R^5$ is $CO_2C_{0-2}$alkylene-aryl, or $CO_2C_{0-2}$alkylene-$C_{2-8}$alkene.
15. The catalyst of claim 1, wherein $R^6$ is H or $C_{1-6}$alkyl.
16. The catalyst of claim 1, wherein $R^6$ is $C_{1-6}$alkoxy.
17. The catalyst of claim 1, wherein $R^6$ is O-aryl.
18. A catalyst selected from the group consisting of
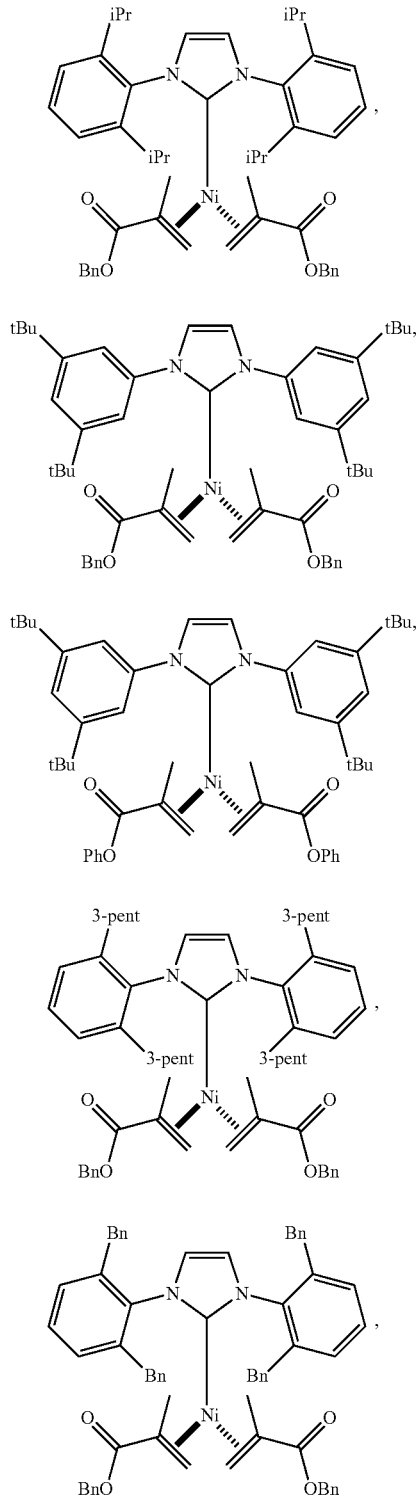
-continued
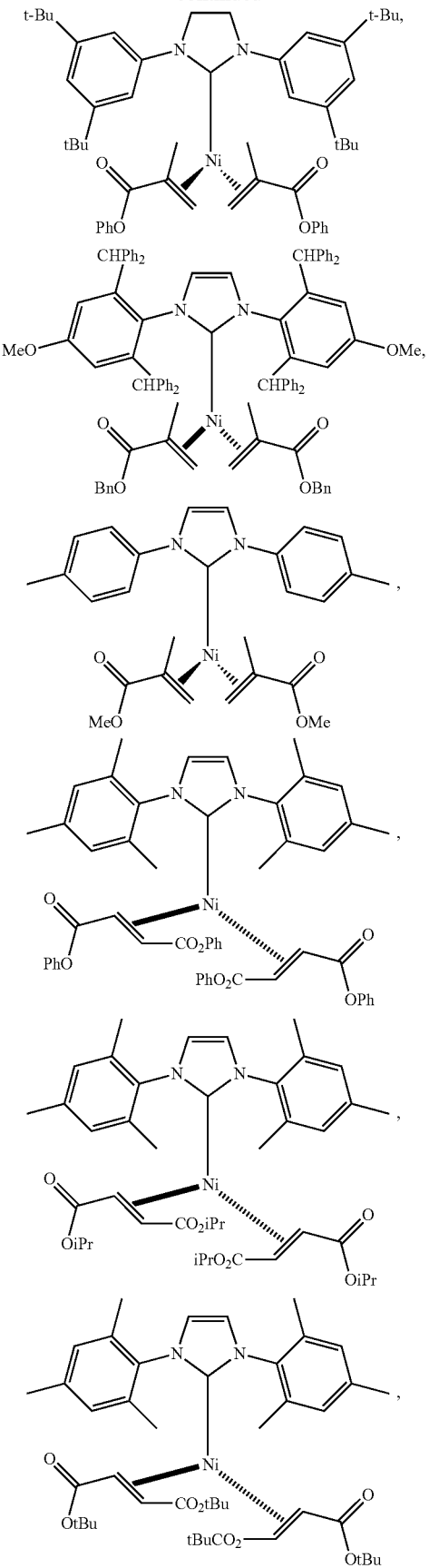

-continued

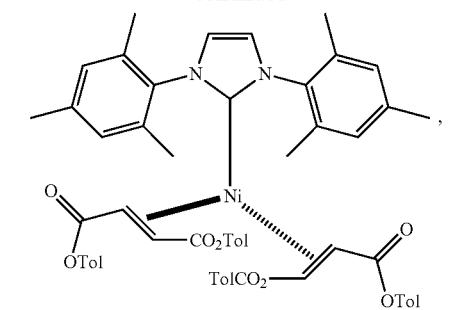

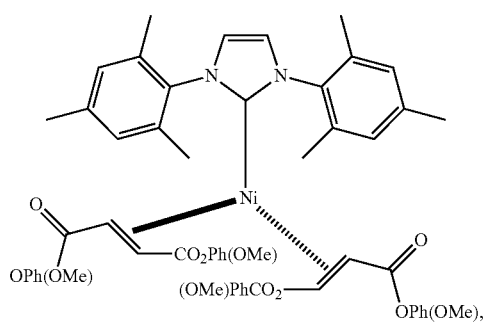

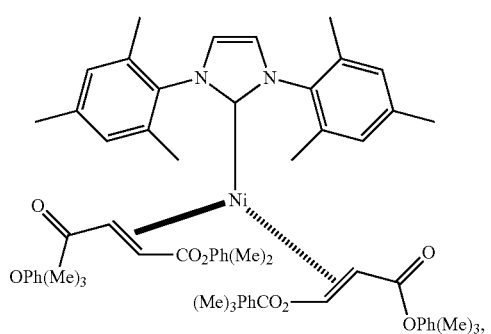

and

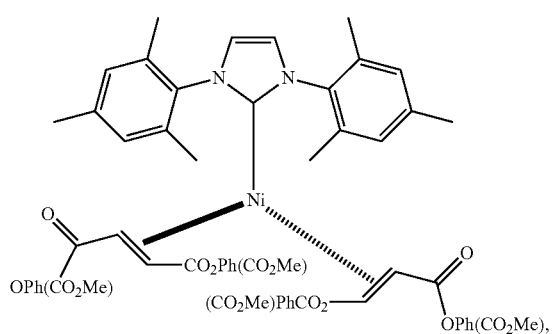

wherein Tol is

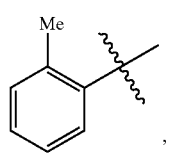

Ph(OMe) is

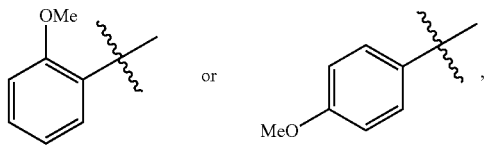 [SMILES: *c1ccccc1OC ; *c1ccc(OC)cc1]

Ph(Me)$_3$ is

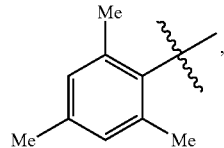

and Ph(CO$_2$Me) is

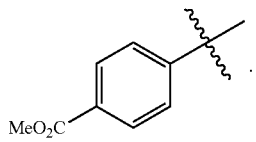

19. A catalyst having a structure of formula (I) or (II):

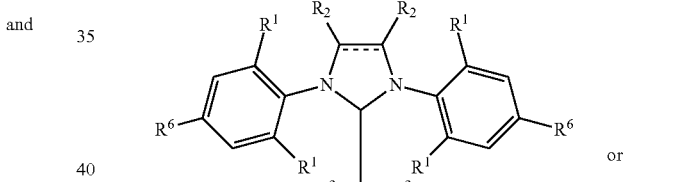

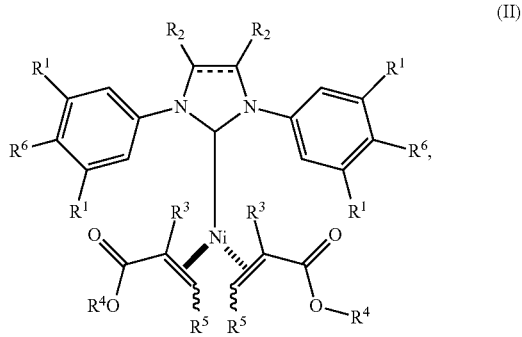

wherein
   the dashed line is an optional double bond;
   each $R^1$ is independently selected from the group consisting of H, $C_{1-8}$alkyl and $C_{1-2}$alkylenearyl;
   each $R^2$ is independently selected from the group consisting of H, halo, $C_{1-3}$alkyl, and aryl, or both $R^2$ together with the carbons to which they are attached form a 6-membered ring;

each $R^3$ is the same and is H, $C_{1-4}$alkyl, or aryl;
each $R^4$ is the same and is $C_{1-6}$alkyl, $C_{0-2}$alkylene-aryl or $C_{0-2}$alkylene-$C_{2-8}$alkene;
each $R^5$ is H; and
each $R^6$ is the same and is H, $C_{1-6}$alkyl, $C_{1-6}$alkoxy, or O-aryl, with the proviso that at least one of $R^1$ and $R^6$ is not H.

20. The catalyst of claim 19, wherein $R^4$ is $C_{0-2}$alkylene-aryl.

* * * * *

UNITED STATES PATENT AND TRADEMARK OFFICE
CERTIFICATE OF CORRECTION

PATENT NO. : 10,486,148 B2  Page 1 of 2
APPLICATION NO. : 15/763468
DATED : November 26, 2019
INVENTOR(S) : John Montgomery et al.

It is certified that error appears in the above-identified patent and that said Letters Patent is hereby corrected as shown below:

In the Claims

At Column 30, Lines 1-12, Claim 18 " 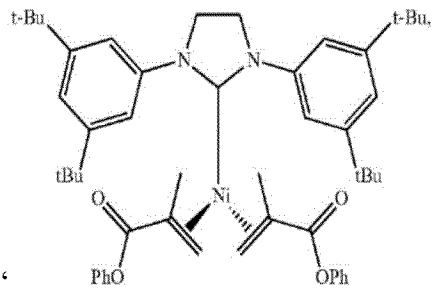 " should be -- 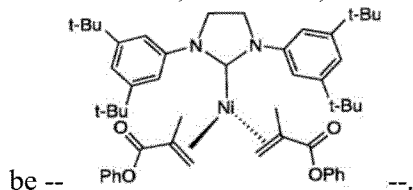 --.

At Column 31, Lines 27-40, Claim 18 " 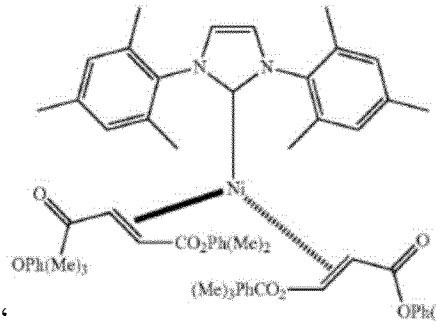 " should

Signed and Sealed this
Twenty-third Day of June, 2020

Andrei Iancu
*Director of the United States Patent and Trademark Office*

CERTIFICATE OF CORRECTION (continued)
U.S. Pat. No. 10,486,148 B2 be --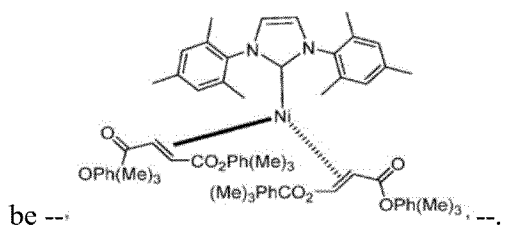, --.